(12) United States Patent
Keen et al.

(10) Patent No.: US 9,582,643 B2
(45) Date of Patent: Feb. 28, 2017

(54) MANAGING USER INFORMATION—SOURCE PRIORITIZATION

(71) Applicant: APPLE INC., Cupertino, CA (US)

(72) Inventors: Daniel S. Keen, San Jose, CA (US); Justin S. Rushing, San Francisco, CA (US); Jay C. Blahnik, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 256 days.

(21) Appl. No.: 14/499,519

(22) Filed: Sep. 29, 2014

(65) Prior Publication Data

US 2015/0347690 A1 Dec. 3, 2015

Related U.S. Application Data

(60) Provisional application No. 62/006,031, filed on May 30, 2014.

(51) Int. Cl.

| | | |
|---|---|---|
| *G06F 17/30* | (2006.01) | |
| *G06F 19/00* | (2011.01) | |
| *G06F 21/62* | (2013.01) | |
| *G06F 9/54* | (2006.01) | |
| *H04L 29/08* | (2006.01) | |
| *H04L 29/06* | (2006.01) | |

(52) U.S. Cl.
CPC ............... *G06F 19/322* (2013.01); *G06F 9/54* (2013.01); *G06F 17/30342* (2013.01); *G06F 17/30386* (2013.01); *G06F 19/30* (2013.01); *G06F 19/323* (2013.01); *G06F 21/6245* (2013.01); *H04L 67/12* (2013.01); *H04L 63/102* (2013.01)

(58) Field of Classification Search
CPC ............... G06F 17/30; G06F 17/30342; G06F 17/30386
USPC ................................... 707/600–899
See application file for complete search history.

(56) References Cited

U.S. PATENT DOCUMENTS

| | | |
|---|---|---|
| 8,157,730 B2 | 4/2012 | Tucker et al. |
| 8,818,823 B2 | 8/2014 | Ackerson et al. |
| 8,930,221 B2 | 1/2015 | Patterson et al. |
| 9,014,779 B2 | 4/2015 | Hutchison et al. |
| 2003/0088520 A1 | 5/2003 | Bohrer et al. |

(Continued)

FOREIGN PATENT DOCUMENTS

WO 2015183495 12/2015

OTHER PUBLICATIONS

U.S. Appl. No. 14/499,449, filed Sep. 29, 2014 by Keen et al.

(Continued)

*Primary Examiner* — Isaac M Woo
(74) *Attorney, Agent, or Firm* — Kilpatrick Townsend & Stockton LLP

(57) ABSTRACT

Systems, methods, and computer-readable medium are provided for managing user information. For example, data of a particular data type may be received from a plurality of sources. In some examples, the data may include at least respective time stamps. The received data may be aggregated to form a data record for a period of time based at least in part on the respective time stamps. Additionally, in some cases, the data record may be provided to at least one application configured to present a user interface representing the aggregated data of the plurality of sources.

20 Claims, 17 Drawing Sheets

(56) References Cited

U.S. PATENT DOCUMENTS

| | | | |
|---|---|---|---|
| 2006/0248592 | A1 | 11/2006 | Agrawal et al. |
| 2009/0320096 | A1 | 12/2009 | Nolan et al. |
| 2010/0306827 | A1 | 12/2010 | Esteve Balducci et al. |
| 2012/0313776 | A1 | 12/2012 | Utter et al. |
| 2013/0030836 | A1 | 1/2013 | Ackerson et al. |
| 2013/0268641 | A1 | 10/2013 | Colbert et al. |
| 2014/0018048 | A1 | 1/2014 | Anand et al. |
| 2014/0059695 | A1 | 2/2014 | Parecki et al. |
| 2014/0135592 | A1 | 5/2014 | Ohnemus et al. |
| 2014/0324469 | A1* | 10/2014 | Reiner .................. G06F 19/322 705/3 |
| 2015/0310174 | A1 | 10/2015 | Coudert et al. |
| 2015/0347499 | A1 | 12/2015 | Keen et al. |
| 2015/0347684 | A1 | 12/2015 | Keen et al. |
| 2015/0347784 | A1 | 12/2015 | Keen |
| 2016/0048695 | A1 | 2/2016 | Cucinotta |

OTHER PUBLICATIONS

U.S. Appl. No. 14/499,461, filed Sep. 29, 2014 by Keen et al.
U.S. Appl. No. 14/499,512, filed Sep. 29, 2014 by Keen et al.
U.S. Appl. No. 62/006,032, filed May 30, 2014 by Kennedy et al.
PCT/US2015/029494, "International Search Report and written opinion," Sep. 23, 2015, 18 pages.
Non-Final Office Action mailed in U.S. Appl. No. 14/499,461 mailed on Aug. 16, 2016. 9 pages.
First Action Interview Pilot Program Pre-Interview Communication mailed Oct. 27, 2016 in U.S. Appl. No. 14/499,449. 5 pages.
Notice of Allowance mailed Dec. 6, 2016 in U.S. Appl. No. 14/499,461. 8 pages.
International Preliminary Report on Patentability mailed on Dec. 15, 2016 in International Application No. PCT/US2015/029494. 16 pages.

* cited by examiner

| 502 | 504 | 506 | 508 | 510 |
|---|---|---|---|---|
| DATA TYPE | VALUE | AUTH REQUEST? | APPROVED? | RESULT ON DATA REQUEST |
| 512 HEART RATE | 78 | YES | YES | 78 |
| 514 GLUCOSE | [ ] | YES | YES | [ ] |
| 516 WEIGHT | 198 | YES | YES | 198 |
| 518 STEPS | 82 | NO | N/A | ERROR |
| 520 TOBACCO | 5 | YES | NO | [ ] |

FIG. 5

MANAGING USER INFORMATION—SOURCE PRIORITIZATION

CROSS REFERENCE TO RELATED APPLICATIONS

The present application claims the benefit of U.S. Provisional Application No. 62/006,031, filed May 30, 2014, entitled "Managing User Information," by Keen, et al. (Ref. No. P23418USP1), which is hereby incorporated by reference for all purposes. The present application is also related to Provisional Application Ser. No. 62/006,032, filed May 30, 2014, entitled "Wellness Aggregator," by Kennedy, et al., the entire contents of which is hereby incorporated by reference as if fully set forth herein, under 35 U.S.C. §120. The present application is also related to Non-Provisional application Ser. No. 14/499,449, filed on the same day herewith, entitled "Managing User Information—Authorization Masking," by Keen, et al., Non-Provisional application Ser. No. 14/499,461, filed on the same day herewith, entitled "Managing User Information—Background Processing," by Keen, et al., and Non-Provisional Application Ser. No. 14/499,512, filed on the same day herewith, entitled "Managing User Information—Data Type Extension," by Keen, et al., the entire contents of each are hereby incorporated by reference as if fully set forth herein, under 35 U.S.C. §120.

BACKGROUND OF THE DISCLOSURE

People are becoming more and more aware of the importance of regular exercise for maintaining one's health. Additionally, a plethora of electronic devices are now available that can track a person's physical activity throughout the day. Such devices can connect or otherwise communicate with other mobile devices, for example, to help track, manage, and/or analyze data associated with the person's physical activity. However, health and activity data continues to be considered extremely personal and often times confidential. As such, developers and device manufacturers continue to identify challenges when providing applications and/or devices for collecting and sharing a user's health information.

BRIEF SUMMARY OF THE DISCLOSURE

Embodiments of the present disclosure can provide systems, methods, and computer-readable medium for managing user information (e.g., personal information collected by one or more external devices). In some examples, a data interchange may be managed that enables and/or allows third-party applications to provide user information to the data interchange and potentially retrieve user information provided by other third-party applications. While managed, the data interchange may be configured to provide access to particular data types of the user data based at least in part on authorization from the user associated with the data.

According to one embodiment, a method may be executed by a computer system to at least identify a particular data type of a plurality of data types to manage. The method may also cause the computer system to receive health data corresponding to the particular data type from at least a first source and a second source of a plurality of data sources. The computer system may receive priority information identifying a priority of the first source and the second source. The method may also cause the computer system to identify a time interval for partitioning the health data by the plurality of data sources. In some examples, the computer system may identify a data entry for the particular data type with a highest identified priority when the data entry exists in a data store configured to maintain the received health data corresponding to the particular data type during each identified time interval over an amount of time. The computer system may also aggregate each identified data entry to form an aggregated record for the particular data type over the amount of time.

In some examples, the method may also cause the computer system to provide the aggregated record to a user device for presentation within a user interface to a user. The method may also cause the computer system to receive a request from the first source for the aggregated record that at least includes the received health data from the second source. The method may also cause the computer system to identify a type of the particular data type based at least in part metadata associated with the received health data. The aggregated record may only include each identified data entry corresponding to the highest identified priority when the identified type is cumulative. The aggregated record may include each identified data entry corresponding to the highest identified priority and other identified data entries for the identified time period when the identified type is discrete.

According to another embodiment, a system may be implemented as a computing device configured with a memory and a processor. The processor may be configured to execute instructions stored on the memory to configure the memory to receive data of a particular data type from a plurality of sources, the data including at least respective time stamps. The processor may also be configured to execute the instructions to aggregate the received data to form a data record for a period of time based at least in part on the respective time stamps. The processor may also be configured to execute the instructions to provide the data record to at least one application configured to present a user interface representing the aggregated data of the plurality of sources.

In some cases, the processor may be further configured to execute the computer-executable instructions to at least identify priority information for at least a subset of the plurality of sources and a time interval for the period of time. The processor may be further configured to execute the computer-executable instructions to at least identify a data entry for the particular data type with a highest identified priority for each time interval. The provided data record may only include each identified data entry corresponding to the highest identified priority when the particular data type is cumulative. In some cases, the at least one application may be a particular one of the plurality of sources, and the data record may include at least one data point not received from the particular one of the plurality of sources. In some examples, at least one of the plurality of sources may comprise a third-party application or a first-party application, and the received data may be based at least in part on metrics collected by a data collection device associated with at least one of the third-party application or the first-party application. The provided data record may include data entries corresponding to the particular data type from the plurality of sources for individual time intervals of the period of time, at least one time interval of the individual time intervals may include a plurality of different data entries, and at least one of the plurality of data entries may be from a different source of the plurality of sources.

According to another embodiment, a computer-readable medium may include instructions that, when executed, configure a computer processor to receive data of a particular data type from at least first data source and a second data source. The instructions may further configure the processor to identify priority information associated with the first data source and the second data source. The instructions may also configure the processor to aggregate, based at least in part on the priority information, the received data to form a data record over a period of time, and provide the data record to at least one application configured to present a user interface representing the aggregated data of the first data source and the second data source.

In some examples, the data record may represent individual data entries of the particular data type for each of a plurality of time intervals during the period of time. A length of the plurality of time intervals may be determined based at least in part on at least one of the particular data type, an activity associated with the particular data type, or historical information associated with a user of the at least one application. Additionally, the identified priority information may be determined based at least in part on at least one of a preference of a user, historical behavior of the user, or activity behavior associated with the first data source or the second data source. The at least one application may comprise a third-party application configured to provide a user interface corresponding to the data record to a user of the third-party application. Additionally, the operations may also comprise providing an application programming interface method to the third-party application for requesting the data record, where the data record may include at least some health information of the user not provided by the third-party application.

BRIEF DESCRIPTION OF THE DRAWINGS

FIG. 5 is simplified data structure diagram illustrating at least some information associated with managing user information as described herein, according to at least one example.

DETAILED DESCRIPTION OF THE DISCLOSURE

Figure 1:
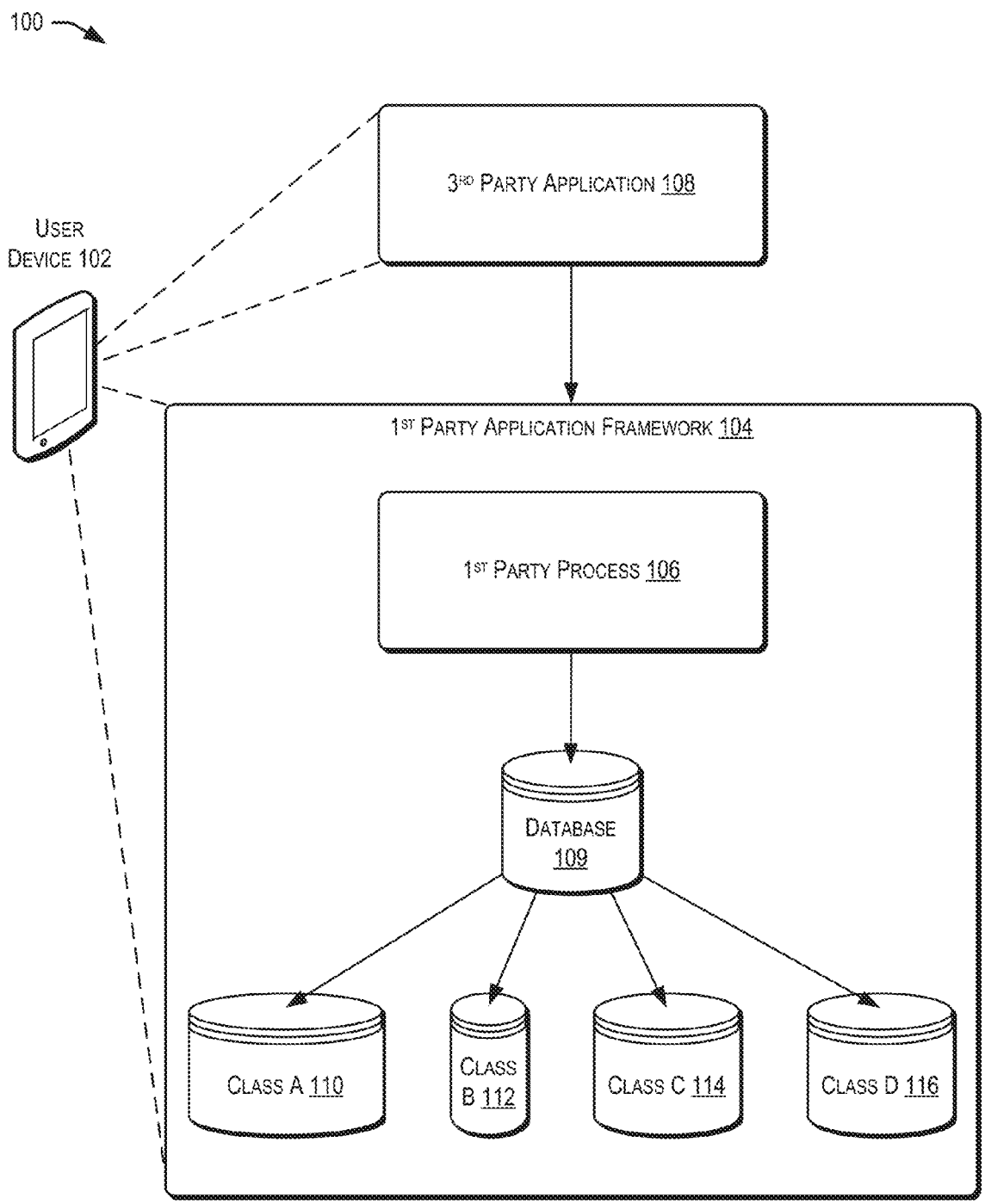
FIG. 1 is a simplified block diagram illustrating an example architecture for managing user information as described herein, according to at least one example.

In the following description, various examples will be described. For purposes of explanation, specific configurations and details are set forth in order to provide a thorough understanding of the examples. However, it will also be apparent to one skilled in the art that the examples may be practiced without the specific details. Furthermore, well-known features may be omitted or simplified in order not to obscure the example being described.

Examples of the present disclosure are directed to, among other things, managing personal information from external sources, or other remote peripheral device of a user. In some examples, the information collected by the data collection devices may be provided to a user device (e.g., a mobile phone, a tablet computer, a laptop computer, a wearable computing device, etc.) and/or one or more first-party or third-party applications of the user device, in some examples, a first-party application may be one that is provided with the operating system (O/S) of the user device, is configured to operate natively with the user device, provided by the developers of the O/S for use with the user device, and/or trusted by the O/S and/or device. Alternatively, a third-party application may be one that is provided by a third-party or entity other than the developer/manufacturer of the user device and/or its O/S. Additionally, in some non-limiting examples, the information being collected and/or managed may be health, fitness, and/or activity information of the user (e.g., blood glucose levels, weight, height, calories burned, heart rate, etc.). The user information may be categorized or otherwise identified by one or more data types (or categories). Weight, number of steps walked, number of calories burned, heart rate, etc., are each an example of a data type. Other data types (e.g., outside of health information) are also envisioned including, but not limited to, hours worked, hourly rate, miles per hour, pages read per minute, etc.

In some cases, a first-party application framework may be executed on a user device that is configured to receive, store, manage, and/or provide such user information to a service provider, to third-party applications, to other first-party applications, and/or to local storage of the user device. As part of the first-party framework, a first-party process may be executed by processors of the user device. The first-party process may include, but is not limited to, a daemon or other background process configured to communicate with the third-party applications, the O/S of the user device, and/or electronic storage of the user device, in some instances, first-party process may be configured to manage a data interchange for sharing some user data with third-party applications. In this way, the first-party process may enable third-party applications to access user information that was initially provided by the third-party application, a first-party application, or other third-party applications. However, as noted, health information of a user may be considered extremely personal and/or confidential; thus, the user may be given the ability to protect or otherwise not share some of the heath information with some, any, or all of the third-party applications (even the ones that provided the health information to the first-party process initially). As such, each third-party application may be instructed to request authorization for accessing particular (or all) data types from the data interchange.

In some examples, when a third-party application requests authorization to access one or more data types of a user's information, the first-party process may be configured to mask whether the user has granted the authorization request. In other words, the third-party application may not be able to identify whether the user has granted authorization or whether the user has not entered data for that data type. In some examples, this masking may be implemented by providing the same response (e.g., an empty or null result) in either case. That is, the first-party process may instead indicate to the third-party application that the authorization request was provided to the user, and not indicate the user's response. Thus, if the user has not provided a data entry for the weight data type, the third-party application may receive a null result when attempting to retrieve that data type. Similarly, if the use has provided their weight, but has not authorized access to the third-party application, when the user's weight is requested, the first-party process may also provide a null or empty result (even though a data entry for that data type exists).

In other examples, third-party applications may be able to subscribe to certain data types, and the first-party process may be configured to automatically wake up the third-party application (e.g., in the background) and ensure that the third-party application is able to process the data. For example, a third-party application of the user may subscribe to a blood pressure data type and indicate an associated subscription frequency. Based at least in part on that frequency, when a new blood pressure reading is received by the first-party process, the process may wake up the appropriate third-party application background, provided with the new data and provide it with the updated data. The process may then wait for confirmation that the third-party application has processed the data. If the process does not receive the confirmation within a specified time, the process may again launch the third-party application, provide the data, and wait for confirmation. In this way, the process can ensure that the third-party application receives the data even if the user has not explicitly requested it.

In at least some aspects, a plug-in framework may be utilized to implement data types that are initially available for use by the first-party process and/or registered third-party applications. Plug-ins of the plug-in framework may register new data types that adhere to different identifiers so they can store their own data in the database automatically.

In some examples, the plug-ins may be implemented as code that can read application programming interface (API) method calls with identifiers and/or strings associated with the data types. Further, by utilizing an asset download, a service provider may enable the addition of new data types not initially provided with the first-party process (e.g., on demand). As such, the service provider may identify one or more data types not initially implemented within the first-party framework that are being requested by users/developers. The service provider may publish information about the new data type and/or how to utilize it. Additionally, the service provider may provide data to the user device for the first-party process to interpret. Once interpreted, and registered with the process, the plug-ins may be utilized to implement these new data types.

In other examples, multiple different third-party applications (e.g., each in communication with a data collection device) may provide user data to the first-party process. For example, a step counter may provide data to an associated third-party application. This third-party application may provide step information to the first-party process. Additionally, the user may utilize a second type of data collection device that also provides step information about the user to a different third-party application. In this case, the user may be enabled to provide priority information to the process such that the process is able to aggregate the step information from the two sources in a meaningful way. The data may be aggregated from a statistical perspective (e.g., to determine the actual number of steps walked by the user) and/or the data may be aggregated to provide a user interface (UI) that helps the user visualize the number of steps they walked. In some cases, the priority information may identify which data (e.g., from which source) to use when there are multiple data entries for the same point in time. In some examples, the source with the highest priority may be rendered when there is overlap in cumulative data (e.g., steps walked are cumulative because they can be summed to a total). In other examples, discrete data may be collected and presented in a way that shows the multiple different data entries for each point in time. For example, weight is an example of a discrete data type because one's weight would not be summed over the day to determine a total weight.

FIG. 1 illustrates a simplified architecture diagram 100 depicting a user device 102 configured to implement a first-party application framework 104. As noted above, the first-party application framework 104 may be configured as an application framework for managing user data of a plurality of data collection devices. While health data is used as an example throughout much of this disclosure, any type of data that may be collected or otherwise provided about a user may be managed by the first-party application framework 104. In some examples, because the first-party application framework 104 is provided or otherwise controlled by developers of the user device 102 and/or its associated O/S, the first-party application framework 104 may be considered a trusted framework with full access to all user data. In some examples, the first-party application framework 104 may be configured with one or more processes executed by the user device 102. For example, a first-party process 106 may be executed in the background such that the user is not aware that it is running. In this way, the first-party application framework 104 may be able to manage the user data whenever desired without interfering with the everyday use of the user device 102. Additionally, in this way, the first-party application framework 104 may be able to communicate with one or more third-party applications 108, also without interruption of the user's use of the user device 102.

In some examples, the first-party process 106 may be configured to manage (e.g., store, retrieve, encrypt, etc.) user data via a database 109 of the user device 102. As part of the first-party application framework 104, the database 109 may be divided or otherwise logically separated into a plurality of classes of data stores. For example, the user data may be stored in at least one of a class A data store 110, a class B data store 112, a class C data store 114, and/or a class D data store. In some examples, the class A data store 110 may be configured to store personally identifiable user information (e.g., personal health, fitness, or activity data). In some examples, this data is only available to the third-party application 108 when the user device 102 is unlocked. By way of example only, the user device 102 may be unlocked when the user associated with the user device 102 has correctly entered his or her user identifier (ID) and password (e.g., when logging in and/or unlocking the lock screen). In some aspects, the class B data store 112 may be configured to store "journal" type data. Journal data may include, but is not limited to, personally identifiable user information and/or other metrics associated with use of one or more data collection devices and/or the third-party application 108. When the user device 102 is locked, the journal data of the class B data store 112 may be inaccessible to the third-party application 108. However, in some examples, data from a data collection device or an application (e.g., the third-party application 108) may be read from or written to the class B data store 112 by the first-party process 106 while the device is locked as long as the first-party process 106 is active. If, however, the first-party process 106 fails or otherwise becomes inactive in the process of reading or writing data to the class B data store 112, the data may become permanently inaccessible, and new data may not be written to the class B data store 112 until the first-party process 106 and/or a new session of the third-party application 108 have relaunched. In this way, the data of the class B data store remains securely accessible because it is only accessible to the first-party process 106 while receiving data from a third-party application 108 during the active session, and no other applications can read that data.

In some aspects, the class C data store 114 may be configured to store metadata associated with the management of the user health, fitness, and/or activity data. This metadata, in some cases, may only be accessible after the first unlock of the user device 102. As such, if the user device 102 reboots (based at least in part on a software issue or a loss of battery power), this data may not be available until the user unlocks at least once. In some aspects, this may prevent jailbreaking or other hacking techniques from accessing this data. The metadata stored in the class C data store 114 may include subscription information, access permission information, and/or safe metadata, but may not, in some examples, identify or be directly associated with any health information (e.g., the data stored in the class A data store 110). The class D data store 116 may be configured to store free-form (e.g., unstructured) information provided by the user. In some examples, this may be health data; however, it may not be updatable and/or linked to any third-party applications (e.g., the third-party application 108) or data collection devices. The class D data may always be available to the first-party process 106 and/or the third-party application 108. In some aspects, the class D data may be pre-filled using information from the third-party application 108 and/or one or more other applications or processes. However, the user may be able to enter additional data, update the data, include incorrect data, or otherwise configure the information in the class D data store 116 as they see fit. The class D data may be available on the lock screen of the user device 102 without anyone (e.g., the user) logging in or otherwise unlocking the user device 102. In this way, the lock screen or another accessible screen of the user device 102 may be analogous to a medical ID bracelet. In some cases, an emergency icon or other function on the lock screen may enable the presentation or rendering of the class D data upon request for anyone (e.g., an emergency medical technician or the like) to see. Further, in some aspects, the third-party application 108 may not have access to the class D data, in part because it may be unstructured data that would be difficult for the third-party application 108 to process.

Figure 2:
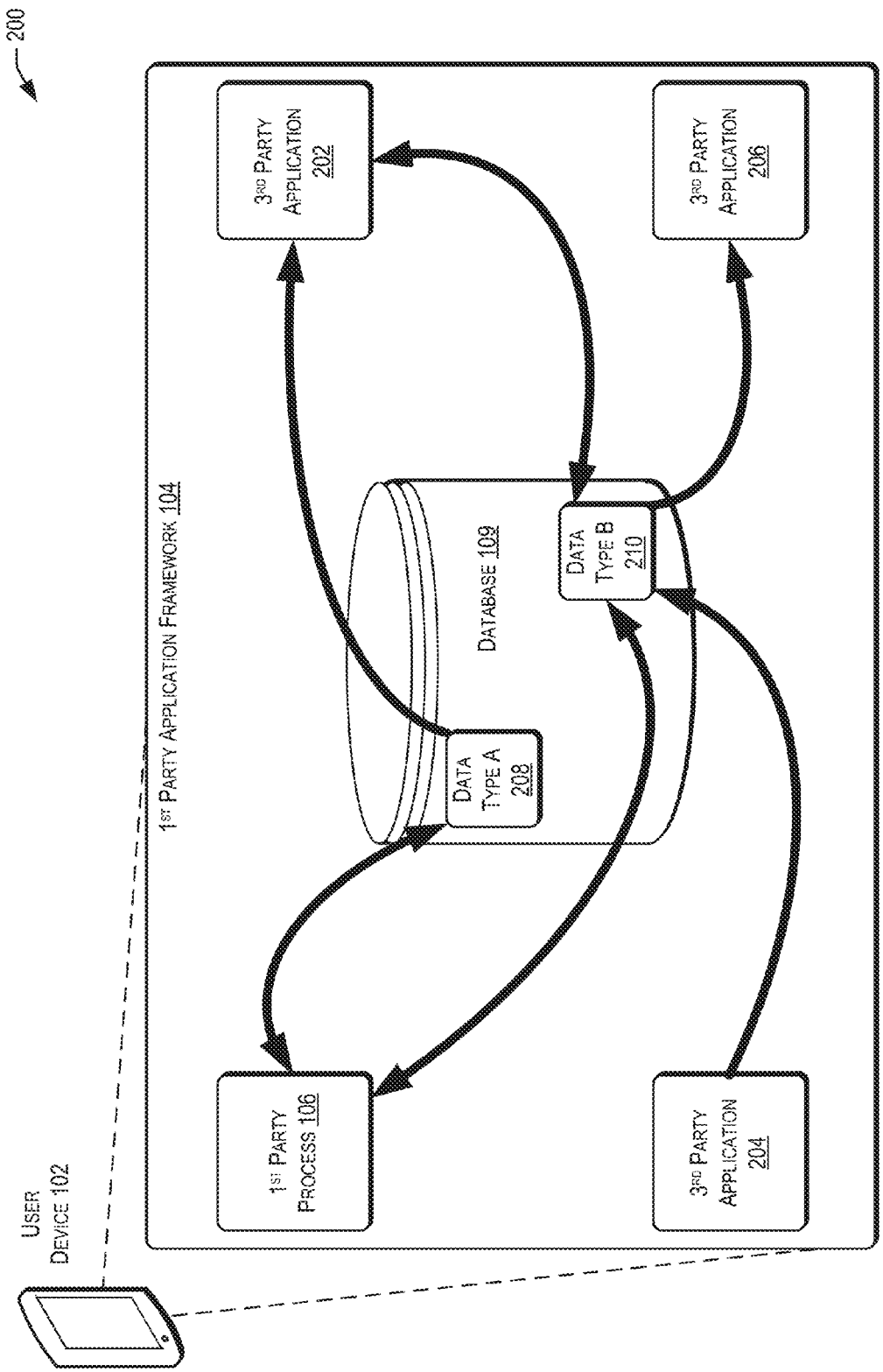
FIG. 2 is another simplified block diagram with connection flows illustrating at least some features of managing user information as described herein, according to at least one example.

FIG. 2 illustrates a simplified architecture diagram 200 depicting additional implementation details associated with the first-party application framework 104 and how user data stored in the database 109 can be accessed by the first-party process 106 and/or one or more different third-party applications 202, 204, 206 (e.g., the third-party application 108). In some examples, as noted above, the database 109 may allow the first-party process 106 and/or the third-party applications 202, 204, 206 to write health and medical data into the database 109 and read it back out. In various aspects, the third-party applications 202, 204, 206 may actually populate the database 109 with data more than the first-party process 106. Thus, the first-party application framework 104 may be configured to act as a data interchange between the applications.

The database 109 may be configured to store data of various different data types. For example, the database 109 may store data corresponding to data type A 208 and/or data type B 210. In some examples, only certain data types may be accessed by certain applications. Thus, some data types may be read only for certain applications, inaccessible to other applications, yet fully accessible to yet other applications. The database 109 may be configured to store at least the following data types: weight, steps, blood pressure, heart rate, tobacco, glucose levels, others described herein, or the like. In one non-limiting example, the first-party process 106 may have read and write access to both data type A 208 and data type B 210. However, the third-party application 204 may only have write access to data type B 210. Additionally, while the third-party application 202 may only be able to read data type A 208, it may have both read and write access to data type B 210. Further, in some examples, the third-party application 206 may only be able to read data type B 210. However, any of these examples may be updated, changed, or otherwise configured by the user and/or by the first-party process 106. As noted, the metadata that identifies which application has which type of access to which data type may be stored in the class C data store 114 of FIG. 1.

Figure 3:
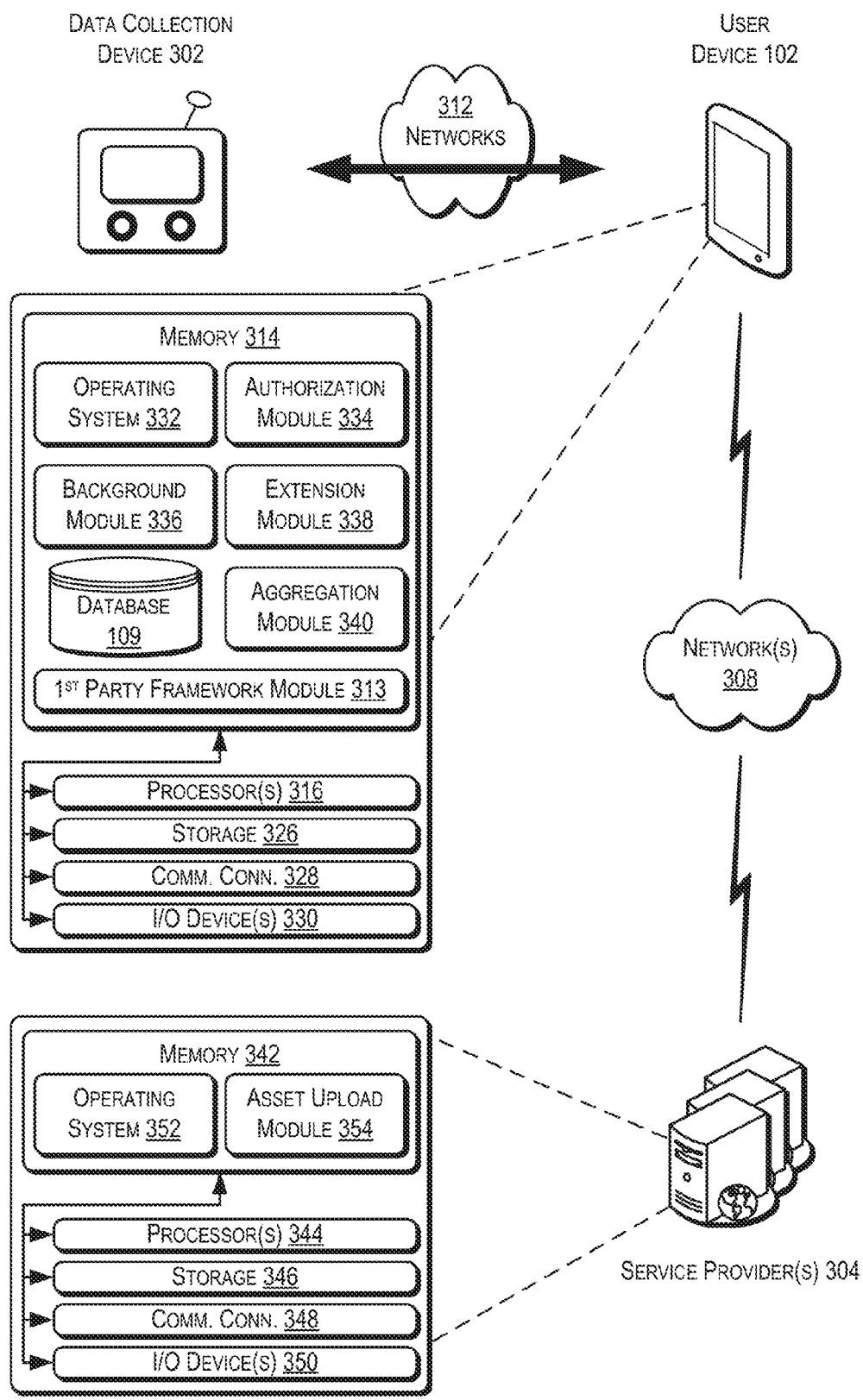
FIG. 3 is another simplified block diagram illustrating another example architecture for managing user information as described herein, according to at least one example.

FIG. 3 illustrates an example architecture 300 for implementing the management of personal information from external sources that includes the user device 102 of FIG. 1 as well as a data collection device 302 and one or more service provider computers 304. In some examples, the devices may be connected via one or more networks 308 and/or 312 (e.g., via Bluetooth, WiFi, or the like). In architecture 300, one or more users may utilize the user device 102 to manage, control, or otherwise utilize one or more data collection devices 302, via one or more networks 312.

In some examples, the networks 308, 312 may include any one or a combination of many different types of networks, such as cable networks, the Internet, wireless networks, cellular networks, satellite networks, other private and/or public networks, or any combination thereof. While the illustrated example represents the user 102 accessing the service provider computers 304 via the networks 308, the described techniques may equally apply in instances where the user device 102 interacts with the service provider computers 304 over a landline phone, via a kiosk, or in any other manner. It is also noted that the described techniques may apply in other client/server arrangements, as well as in non-client/server arrangements (e.g., locally stored applications, peer to peer configurations, etc.).

As noted above, the user device 102 may be configured to manage a data interchange for reading and/or writing user data to the database 109, and for sharing that user data among one or more authorized third-party applications. In some examples, the data collection device 302 may be configured to provide health, fitness, activity, and/or medical data of the user to a third- or first-party application (or process). In turn, this data may be shared, aggregated, and/or accessed via the first-party framework module 313 that may be configured to implement the first-party application framework 104 of FIG. 1. The user device 102 may be any type of computing device such as, but not limited to, a mobile phone, a smartphone, a personal digital assistant (PDA), a personal computer (e.g., laptop or desktop), a thin-client device, a tablet computer, an electronic book (e-book) reader, a wearable device, etc. In some examples, the user device 102 may be in communication with the service provider computers 304 and/or the data collection device 302 via the networks 308, 312, or via other network connections.

In one illustrative configuration, the user device 102 may include at least one memory 314 and one or more processing units (or processor(s)) 316. The processor(s) 316 may be implemented as appropriate in hardware, software (e.g., computer-executable instructions, firmware, etc), or combinations thereof. Computer-executable instruction or firmware implementations of the processor(s) 316 may include machine-executable instructions written in any suitable programming language to perform the various functions described. The user device 102 may also include goo-location devices (e.g., a global positioning system (GPS) device or the like) for providing and/or recording geographic location information associated with the user device 102.

The memory 314 may store program instructions that are loadable and executable on the processor(s) 316, as well as data generated during the execution of these programs. Depending on the configuration and type of user device 102, the memory 314 may be volatile (e.g., random access memory (RAM)) and/or non-volatile (e.g., read-only memory (ROM), flash memory, etc.). The user device 102 may also include additional removable storage and/or non-removable storage including, but not limited to, magnetic storage, optical disks, etc. The disk drives and their associated non-transitory computer-readable media may provide non-volatile storage of computer-readable instructions, program modules, data structures, and other data for the computing devices. In some implementations, the memory 314 may include multiple different types of memory, such as RAM, static random access memory (SRAM), dynamic random access memory (DRAM), or ROM. While the volatile memory described herein may be referred to as RAM, any volatile memory (e.g., that does not maintain data stored therein once unplugged from a host and/or power) would be appropriate.

The memory 314 and the additional storage 326, both removable and non-removable, are all examples of non-transitory computer-readable storage media. For example, non-transitory computer readable storage media may include volatile or non-volatile, removable or non-removable media implemented in any method or technology for storage of information such as computer-readable instructions, data structures, program modules, or other data. The memory 314 and the additional storage 326 are all examples of non-transitory computer storage media. Additional types of computer storage media that may be present in the user device 102 may include, but are not limited to, phase-change RAM (PRAM), SRAM, electrically erasable programmable read-only memory (EEPROM), flash memory, compact disc read-only memory (CD-ROM), digital video disc (DVD), magnetic cassettes or tape, magnetic disk storage, or any other medium that can be used to store the desired information and that can be accessed by the user device 102. Combinations of any of the above should also be included within the scope of non-transitory computer-readable media. Alternatively, computer-readable communication media may include computer-readable instructions, program modules, or other data transmitted within a data signal, such as a carrier wave, or other transmission. However, as used herein, computer-readable storage media does not include computer-readable communication media.

The user device 102 may also contain communications connection(s) 328 that allow the user device 102 to communicate with a data store (e.g., the database 109), or another computing device via the networks 308, 312. The user device 102 may also include I/O device(s) 330, such as a keyboard, a mouse, a pen, a voice input device, a touch input device, a display, speakers, etc.

Turning to the contents of the memory 314 in more detail, the memory 314 may include an operating system 332 and/or one or more application programs or services for implementing the features disclosed herein including an authorization module 334, a background module 336, an extension module 338, and/or an aggregation module 340. In some examples, the authorization module 334 may be configured to manage authorization requests from third-party applications for access of user data stored in the database 109 (e.g., class A data of FIG. 1). The authorization module 334 may also be configured to mask when a user denies authorization to a third-party application for a particular data type. In this way, the third-party application may not be able to infer anything about the user based at least in part on the denial. The background module 336 may be configured to launch and/or relaunch third-party applications in as background process. In some examples, the background module 336 may also be configured to verify that the third-party application has finished processing the data it requested, by continuing to relaunch the third-party application in the background until notification is received that the third-party application has completed processing. The extension module 338 may be configured to handle registering new data types with the first-party framework module in order to extend the functionality of the first-party application framework 104 of FIG. 1. Further, the aggregation module 340 may be configured to aggregate or otherwise combine (and, in some examples, provide presentation for) user data received from multiple different data sources.

The service provider computers 304 may also be any type of computing device such as, but not limited to, a mobile phone, a smartphone, PDA, a personal computer, a thin-client device, a tablet computer, an e-book reader, a wearable device, etc. In some examples, the service provider computers 304 may be in communication with the user device 102 and/or the data collection device 302 via the networks 308, 312, or via other network connections.

In one illustrative configuration, the service provider computers 304 may also include at least one memory 342 and one or more processing units (or processor(s)) 344. The processor(s) 344 may be implemented as appropriate in hardware, computer-executable instructions, firmware, or combinations thereof. Computer-executable instruction or firmware implementations of the processor(s) 344 may include computer-executable or machine-executable instructions written in any suitable programming language to perform the various functions described.

The memory 342 may store program instructions that are loadable and executable on the processor(s) 344, as well as data generated during the execution of these programs. Depending on the configuration and type of service provider computer 304, the memory 342 may be volatile (such as RAM) and/or non-volatile (such as ROM, flash memory, etc.). The service provider computer 304 may also include additional removable storage and/or non-removable storage 346 including, but not limited to, magnetic storage, optical disks, and/or tape storage. The disk drives and their associated non-transitory computer-readable media may provide non-volatile storage of computer-readable instructions, data structures, program modules, and other data for the computing devices. In some implementations, the memory 342 may include multiple different types of memory, such as SRAM, DRAM, or ROM. While the volatile memory described herein may be referred to as RAM, any volatile memory that would not maintain data stored therein once unplugged from a host and/or power would be appropriate. The memory 342 and the additional storage 346, both removable and non-removable, are all examples of non-transitory computer-readable storage media.

The service provider computer 304 may also contain communications connection(s) 348 that allow the service provider computer 304 to communicate with a data store (e.g., the database 109 of the user device 102 or another database), or another computing device via the networks 308, 312. The service provider computer 304 may also include I/O device(s) 350.

Turning to the contents of the memory 342 in more detail, the memory 342 may include an operating system 352 and/or one or more application programs or services for implementing the features disclosed herein including an asset upload module 354. In some examples, the asset upload module 354 may be configured to manage mobile assets and/or prepare or otherwise generate information for enabling the user device 102 and/or the first-party framework module 313 to extend the data types originally configured within the first-party application framework. 104 of FIG. 1. For example, the asset upload module 354 may be configured to identify one or more new data types and generate data to be provided to the user device 102 for registering or otherwise effectuating the new data types.

Figure 4:
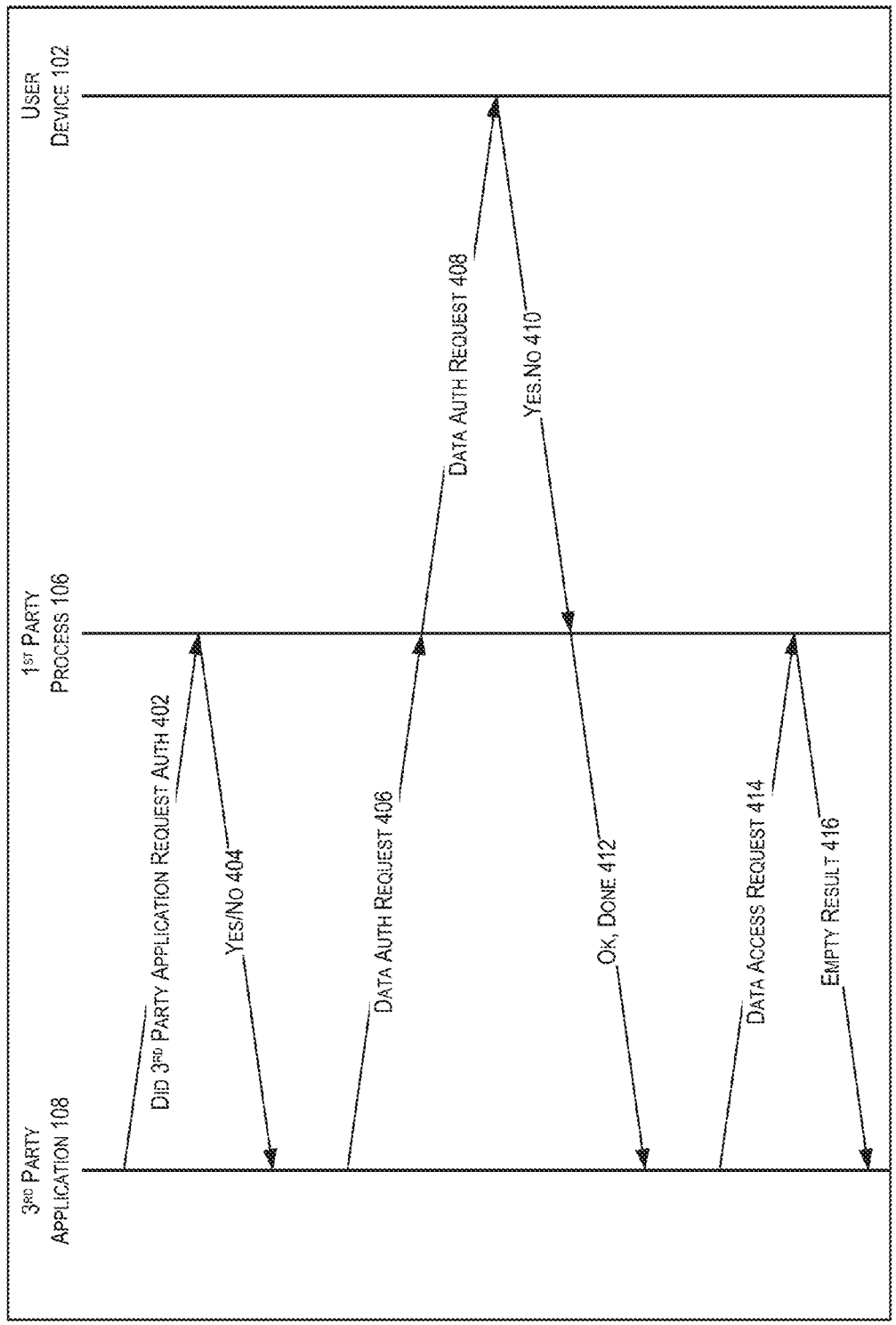
FIG. 4 is a sequence diagram illustrating additional features of managing user information as described herein, according to at least one example.

FIG. 4 illustrates an example flow diagram 400 for describing additional features of the management of user data from a data collection device as described herein. 111 at least one non-limiting example, the flow 400 may be implemented, at least in part, by the authorization module 334 described above with reference to FIG. 3. As such, the flow 400 may be from the perspective of the first-party process 106 residing on the user device 102 of FIG. 1. Communication may be between the first-party process 106 and the third-party application 108 of FIG. 1 or between the first-party process 106 and any of the third-party applications 202, 204, 206 of FIG. 2, or any other applications. In some examples, the first-party process 106 may receive a request 402 from the third-party application 108. The request may be an attempt to identify whether the third-party application has requested authorization for a particular data type. For example, the third-party application may want to know whether it had already requested authorization for blood glucose levels, or weight, from the first-party process 106. At 404, the first-party process 106 may respond with a "yes" or a "no."

In some examples, the third-party application 108 may end here, if they have already requested authorization for the particular data type. Additionally, in some examples, the request at 402 may be for all data types, as opposed to a particular data type. In other examples, if the third-party application 108 has not yet requested authorization for one, some, or all of the data types, the first-party process 106 may receive an authorization request 406. As noted above, the authorization request may be a set of data types, all the data types available (e.g., to limit the number of these requests 406), or a particular data type. Once received by the first-party process 106, the first-party process 106 may forward this request to the user of the user device 102 (e.g., via a UI provided to the user). At 410, the first-party process 106 may receive a response from the user indicating whether the user has authorized access to that third-party application 108. The answer may be different for each data type and/or for each third-party application. For example, and as noted in FIG. 3, each application may have different access restrictions for different data types. Independent of whether the user responds "yes" or "no" at 410 to the data authorization request 406, the first-party process 106 may provide a response 412 to the first-party process 106 that indicates that the first-party process 106 has provided the data authorization request 408 to the user. In some examples, this response 412 may be a simple "ok, done" response, or any other response that indicates that this step has been completed. However, the response 412 may not indicate whether the user has authorized the access or not. In this way, the authorization grant or denial is masked to the third-party application 108. Future requests 414 for access to this particular data type (e.g., one where access authorization was denied) may receive an empty or null result 416. Additionally, future requests 414 for this data type may receive an empty or null result at 416 when not data value exists, even if the access authorization was granted. A similar flow for write requests is envisioned as well; however, when write access authorization is not granted, the first-party process 106 may provide the last set of data that the third-party application 108 attempted to write. Thus, the third-party application 108 may not be able to tell when read authorization requests are denied or when write authorization requests are denied.

FIG. 5 illustrates an example table 500 of values for demonstrating sample results provided to a third-party application by the first-party process 106 of FIG. 1, for different scenarios. For example, in the table 500, the first column represents data type 502, the second column represents values 504 for that data type received from a third-party application (or entered by a user), the next column represents whether the authorization request was sent 506, the fourth column represents whether the authorization was approved 508 by the user, and the final column represents an example result that would be provided to the requesting third-party application 510 based at least in part on the values of the other columns, per row.

In one non-limiting example, row 512 may represent a scenario for the "heart rate" data type. In this example, the user's heart rate may have been recorded as 78 beats per minute and the requesting application may have already provided an authorization request. Here, the user has approved the authorization request; as such, the result provided to the requesting application will match the value 78. This will even be the case if the application requesting the data value was not the application that provided to the data value to the first-party process 106. In another example, row 514 may represent a scenario for the "glucose" level data type. In this example, the user's glucose levels may not have been recorded. Thus, even though an authorization request has been sent and approved, no data result is available; as such, an empty result is provided to the application. At row 516, a similar scenario as shown in row 512 is depicted but for the "weight" data type. Here, the value in the data store is provided to the requesting application. At row 518, the "steps" (e.g., steps per minute) data type shows a data value of 82. However, since no authorization request has been submitted by the requesting application, there would not have been an approval or a denial; as such, an error would be returned to the requesting application if they attempted to request that data type. Further, row 520 shows a "tobacco" data type that may indicate whether the user is a smoker and, if so, how many cigarettes (or other quantifiable measure) they smoke per day. In some examples, a value of "5" may indicate that the user is a smoker and smokes five cigarettes per day, while a value of "0" may indicate that the user is a non-smoker. Here, the data value indicates that the user is a smoker, and the table 500 indicates that the application has requested access authorization. However, the user has denied the authorization request for this data type (e.g., maybe because this personal health information is not something the user wishes to share with third-party applications). As such, even though a data result exists in the data store, the result provided to the requesting application may be the same as when no value existed. That is, when authorization is denied, the result may be empty. In this way, the denial and approval of authorization requests can be masked by the type of response given to the requesting application.

Figure 6:
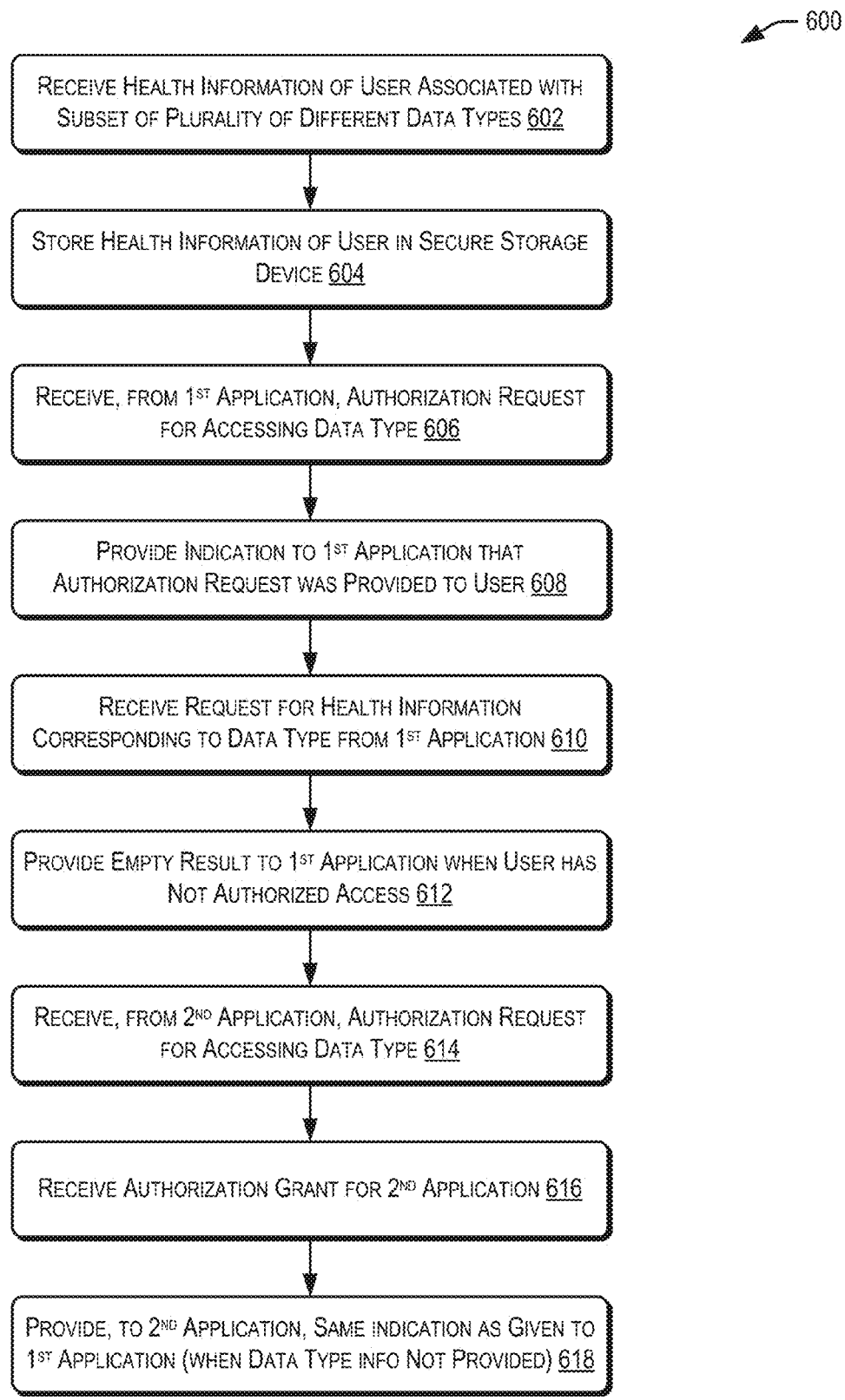
FIG. 6 is a flowchart of a method for managing user information as described herein, according to at least one example.
Figure 7:
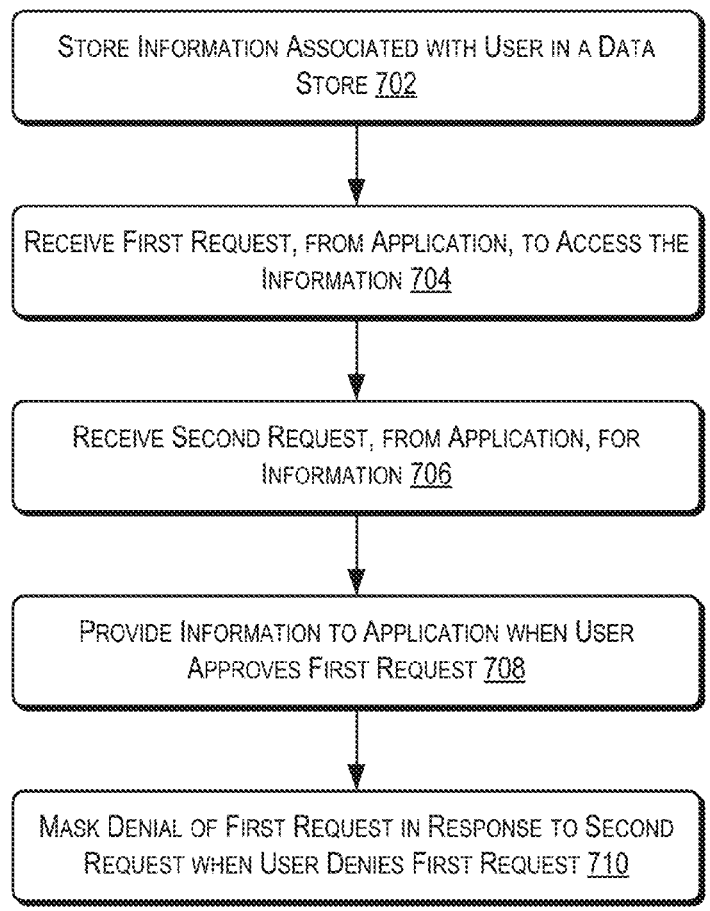
FIG. 7 is another flowchart of a method for managing user information as described herein, according to at least one example.

FIGS. 6 and 7 illustrate example flow diagrams showing processes 500 and 600 for managing personal information from external sources, according to at least a few embodiments. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer-readable storage medium, for example, in the form of a computer program including a plurality of instructions executable by one or more processors.

In some examples, the user device 102 (e.g., utilizing at least the authorization module 334 shown in FIG. 3) may perform the process 600 of FIG. 6. The process 600 may begin at 602 by including receipt of health information of a user associated with a subset of a plurality of different data types. In some examples, this may include receiving a single data entry of health data corresponding to a single data type or a set of data entries of health data corresponding to a single data type each. Additionally, in some cases, the health information may be received from one or more applications (e.g., a third-party application or a first-party application) of the user device 102, and may have initially been collected by a data collection device. At 604, the process 600 may include storing the health information of the user in a secure storage device. For example, the health information may be stored in a database configured to restrict access of the data to particular applications based at least in part on configurable settings, the requesting application, and/or the data type being requested. In some cases, the process 600 may include receiving an authorization request for accessing a data type from a first application at 606. The process 600 may also include providing an indication to the first application that the authorization request was provided to the user at 608.

At 610, the process 600 may include receiving a request for health information corresponding to the data type. This request may be received from the first application. At 612, the process 600 may also include providing an empty result to the first application when the user has not authorized access. In this way, the fact that the user denied the authorization request, the first application is not made of aware of this. In other words, the first application will not know whether the authorization request was denied or whether no data value existed in the data store for that data type. Further, in some examples, the process 600 may include receiving another authorization request for accessing the data type at 614. This request may come from a second application. At 616, the process 600 may include receiving an authorization grant for the second application to access the same data type. In some aspects, the process 600 may end at 618, where the same indication given to the first application may be provided to the second application. That is, the same result (e.g., an empty result) may be provided to the first application when the data type info (e.g., a value) was not provided as is provided to the second application when the data value was provided but authorization was not granted.

FIG. 7 illustrates another process 700 for managing personal information from external sources, according to at least a few embodiments. In some examples, the user device 102 (e.g., utilizing at least the authorization module 334 shown in FIG. 3) may perform the process 700 of FIG. 7. The process 700 may begin at 702 by including storing information associated with a user in a data store. In some examples, the information may be health, fitness, activity, and/or medical information collected from a data collection device (e.g., a WiFi thermometer, scale, heart rate monitor, etc.). At 704, the process 700 may include receiving a first request to access the information. The first request may be received from an application being executed by the user device 102. The first request may also be an access authorization request (e.g., to request access to the information). In some examples, the process 700 may also include receiving a second request from the application for the information at 706. The second request may be an access request, the response to which may depend on whether the user has granted or denied the first request. The process 700 may include providing the information to the application when the user approves the first request at 708. That is, if the user has approved the access authorization request, when the application requests the information, the process 700 may provide it. However, in other examples, the process 700 may end at 710, where denial of the first request (e.g., the authorization request) may be masked at least in response to the second request (e.g., the access request).

Figure 8:
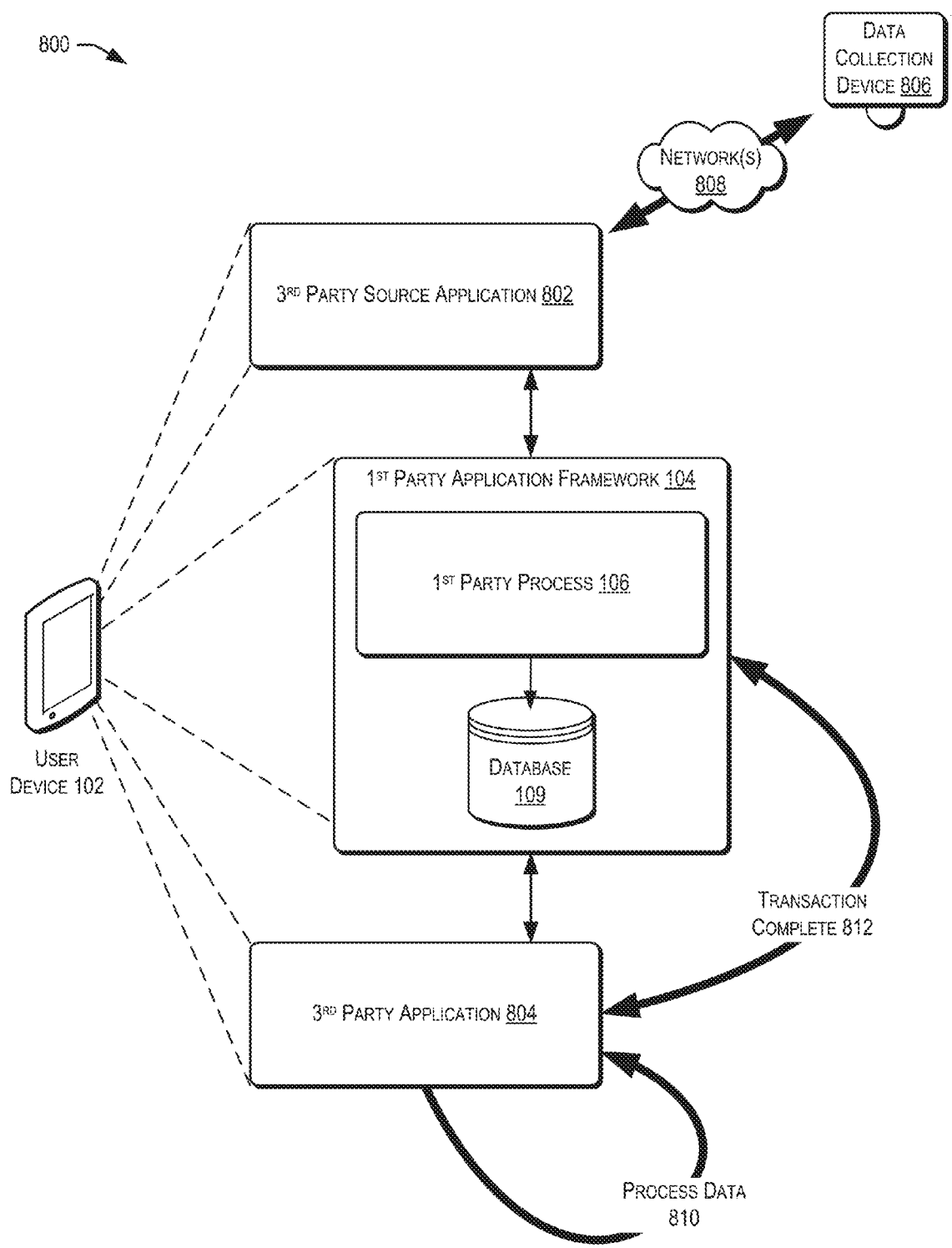
FIG. 8 is another simplified block diagram illustrating another example architecture for managing user information as described herein, according to at least one example.

FIG. 8 illustrates another example architecture 800 for implementing additional features of the management of personal information from external sources, depicting the user device 102, the first-party application framework 104, and the first-part/process 106 of FIG. 1. In some examples, as noted above, one or more third party applications (e.g., third-party source application 802 and/or third-party application 804) may be in communication with the first-party application framework 104 and/or the first-party process 106 for providing user information collected by a data collection device 806. In some examples, the data collection device 806 may be any wearable or mobile device configured to collect activity, health, medical, and/or fitness information about a user. This information may then be provided to one of the third-party applications (e.g., the third-party source application 802 in this example) via one or more networks 808. Once received by the third-party source application 802, the information can be provided to the first-party process 106 for storage in the database 109.

In at least one non-limiting example, the third-party application 804 may be configured to subscribe to one or more data types of the user information stored within the database 109. The third-party application 804 may also include a frequency corresponding to each subscription. In some examples, each subscription may be associated with a different data type and have its own associated frequency. For example, the third-party application 804 may subscribe to the "weight" data type with a frequency of "daily," and also subscribe to the "blood glucose level" data type with a frequency of "immediate." As such, in some examples, the first-party process 106 may launch the third-party application 804 in the background when certain actions occur based at least in part on the subscription, and provide the data to the third-party application 804 while it is launched. For example, whenever the third-party source application 802 provides a new blood glucose reading (assuming the data collection device 806 collects and provides such data), the first-party process 106 may automatically launch the third-party application 804, enable it to request the new reading, and then provide the data to the third-party application 804 based at least in part on the request. In this scenario, the third-party application 804 was launched nearly immediately (e.g., within a second or so) after the new blood glucose reading was received because the subscription frequency was set to "immediate," thus, providing the data (e.g., the new blood glucose reading) nearly immediately. Alternatively, if the new reading had been weight, the third-party application 804 may not have been launched (and the data provided) until the end of the day based at least in part on that subscription being set to "daily."

In some cases, the third-party application 804 may receive the new reading (e.g., the blood glucose reading noted above) and begin to process the data 810. While the processing 810 may be agnostic to the first-party process 106 (e.g., the first-party process 106 may not know what processing 810 is being done with the data reading), the first-party process 106 may be configured to look or otherwise poll fir a transaction complete confirmation 812. In some examples, if the transaction complete confirmation 812 is not received within a particular time period, the first-party process 106 may relaunch the third-party application 804 until the confirmation 812 is received. In other examples, the first-party process 106 may be also be configured to relaunch the third-party application 804 if the third-party application 804 crashes while running in the background. In other words, the first-party process 106 may be configured to repeatedly relaunch the third-party application 804 in the background until the confirmation 810 is received, thus ensuring that the third-party application 804 was able to complete its processing 810. In this way, a virtual service level agreement (SLA) may be provided to the third-party applications based at least in part on the subscription.

In some cases, the frequency may be automatically determined based at least in part on the type of data and/or a historical frequency associated with the data. For example, weight data doesn't generally change that much within a day, so the frequency may be automatically set at daily. Alternatively, blood glucose level can change drastically within a few minutes and can be life threatening. As such, the frequency for a subscription to blood glucose level may be automatically set at "immediate" or every "minute." Additionally, in some examples, the amount of time the first-party process 106 waits before relaunching the third-party application 804 in the background may change between each relaunch. For example, the first-party process 106 may launch the third-party application 804 in the background upon the initial new blood glucose reading (e.g., using the example above) and wait 2 minutes for the third-party application 804 to provide the confirmation 812. If no confirmation 812 is received within the two minute period, the first-party process 106 might relaunch the third-party application 804 and wait a second period of time. In some cases, the period of time that the first-party process 106 waits may increase for each relaunch. An exponential backoff function may be used to determine the wait period bet-seen each relaunch. For example, if the first wait period is two minutes, the second wait period might be four minutes, then eight minutes, and so on. If the day (or a 24 hour period) ends without receiving the confirmation 812, the first-party process 106 may start the cycle over by waiting two minutes each period or it may switch to waiting for amore consistent period of time (e.g., relaunching the third-party application 804 every day). Once confirmation is received, the first-party process 106 may stop relaunching the third-party application 804. However, if the confirmation is never received, the first-party process 106 may continue to relaunch and wait for confirmation 812 until confirmation 812 is eventually received that the processing 810 of the requested data is complete. For certain third-party applications, this continual relaunch may save a user's life.

In some cases, the first-party process 106 may not be configured to provide the activity and/or health data to the third-party application 804 when the user device 102 is locked (e.g., if that data is stored in the class A data store 110). This configuration may be based at least in part on privacy and/or security restrictions. Thus, some third-party applications 804 that are subscribed to certain data types may not be able to receive data if the device 102 is locked (typically because most health and/or activity data is stored in the class A data store 110). Even if the third-party application 804 is able to be launched, it is possible that the first-party process 106 may not be able to send the data. However, in some cases, when a third-party application is subscribed to a data type, the corresponding data may instead be stored in the class C data store 114 so that it can be served even with the user device 102 is locked. Once confirmation of the completed transaction 812 is received, the first-party process 106 may remove or otherwise delete the corresponding data from the class C data store 114 and/or move the corresponding data to the class A data store 110. Alternatively, or in addition, if the corresponding data is stored in the class A data store 110, and the user device 102 is locked, a notification or alert may be provided on the lock screen that indicates that data is waiting to be sent to a third-party application 802, but that the data cannot be sent until the device 102 is unlocked. Once unlocked, the device 102 can provide the corresponding data from the class A data store 110.

Figure 9:
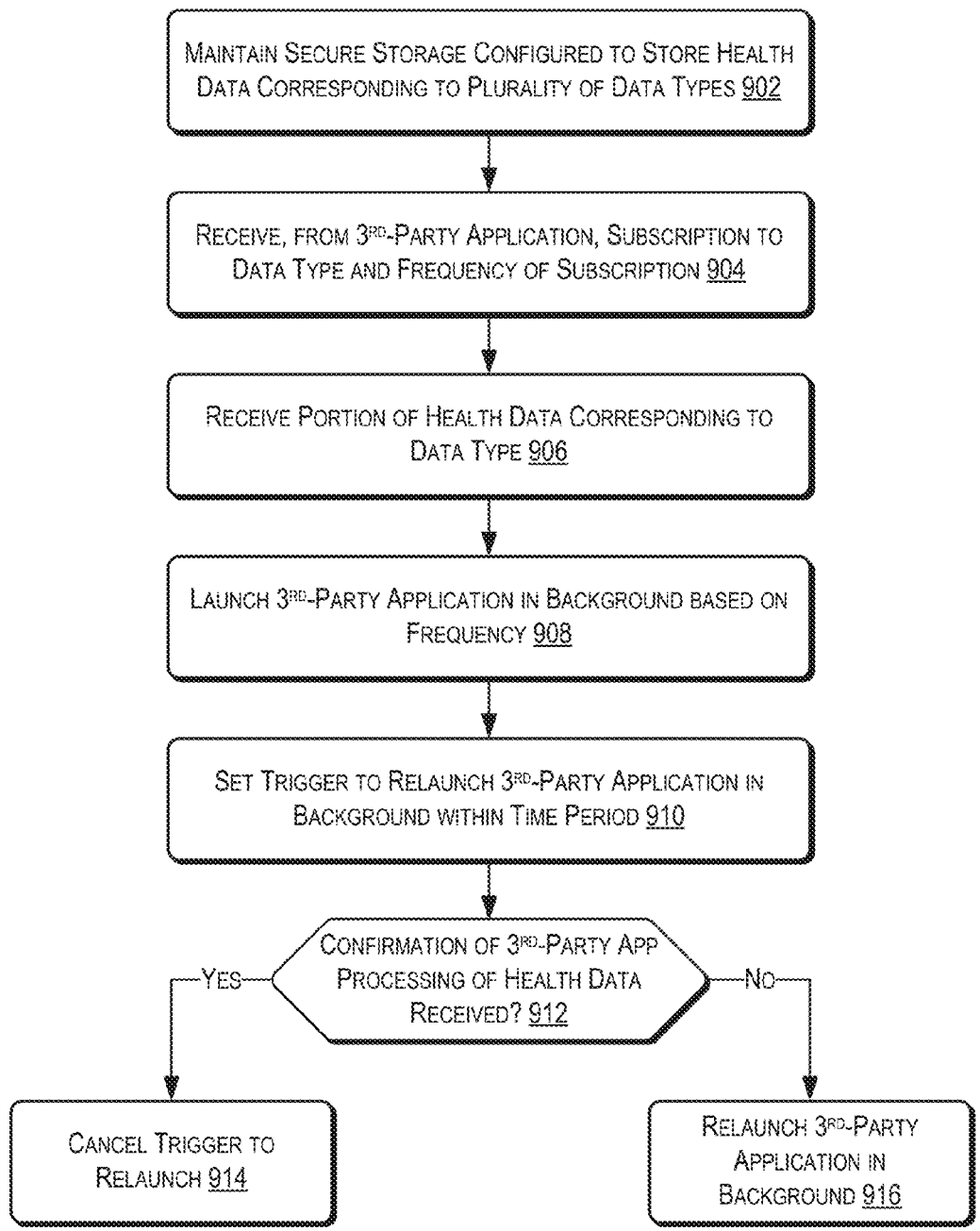
FIG. 9 is another flowchart of a method for managing user information as described herein, according to at least one example.
Figure 10:
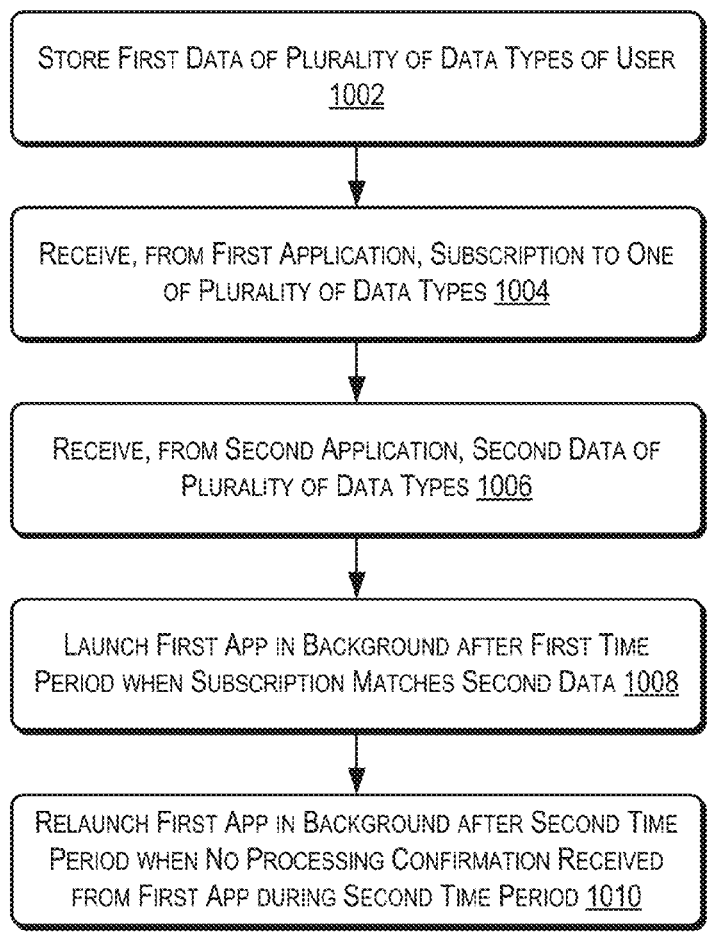
FIG. 10 is another flowchart of a method for managing user information as described herein, according to at least one example.

FIGS. 9 and 10 illustrate example flow diagrams showing processes 900 and 1000 for managing personal information from external sources, according to at least a few embodiments. In some examples, the user device 102 (e.g., utilizing at least the background module 336 shown in FIG. 3) may perform the process 900 of FIG. 9. The process 900 may begin at 902 by including maintenance of a secure storage device configured to store health data corresponding to a plurality of data types. In some examples, the secure data store may be configured similar to the database 109 described above with reference to FIG. 1 (e.g., including class A, B, C, and/or D types of data). At 904, the process 900 may include receiving, from a third-party application, a subscription to a data type and a frequency of the subscription. The process 900 may also include receiving a portion of health data corresponding to the data type at 906. For example, the first-party process 106 of FIG. 1 may receive weight data, heart rate information, etc, of a user. At 908, the process 900 may include launching the third-party application in the background based at least in part on the frequency associated with the subscription. Additionally, in some examples, the process 900 may include setting a trigger to relaunch the third-party application in the background within a time period at 910. As noted, the time period may be configurable (e.g., by the first-party process 106, the third-party application, and/or a user) and/or may be implemented using an exponential backoff algorithm or other method systematically changing the time period between relaunches. In some examples, the trigger may correspond to the time period and/or an event (e.g., receipt of the confirmation described above). Additionally, setting the trigger may include identifying the triggering event (e.g., receipt of the confirmation or tolling of a time period). At 912, the process 900 may include determining whether confirmation of the third-party application processing is received. If the confirmation is received, the process 900 may end at 914, where the process 900 may cancel the trigger (e.g., close the polling loop that looks for the time period to end or the confirmation to be received). Alternatively, if the confirmation is not received, the process 900 may end at 916, where the process 900 may relaunch the third-party application in the background and continue to wait for the confirmation.

FIG. 10 illustrates another process 1000 for managing personal information from external sources, according to at least a few embodiments. In some examples, the user device 102 (e.g., utilizing at least the background module 336 shown in FIG. 3) may perform the process 1000 of FIG. 10. The process 1000 may begin at 1002 by including storage of first data of a plurality of data types of a user. At 1004, the process 1000 may include receiving, from a first application, a subscription to one of the plurality of data types. The process 1000 may also include receiving, from a second application, second data of the plurality of data types at 1006. Additionally, in some examples, at 1008, the process 1000 may include launching a first application in the background after a first time period when the subscription matches the second data. At 1010, the process 1000 may end by relaunching the first application in the background after a second time period when no processing confirmation is received from the first application during the second time period.

Figure 11:
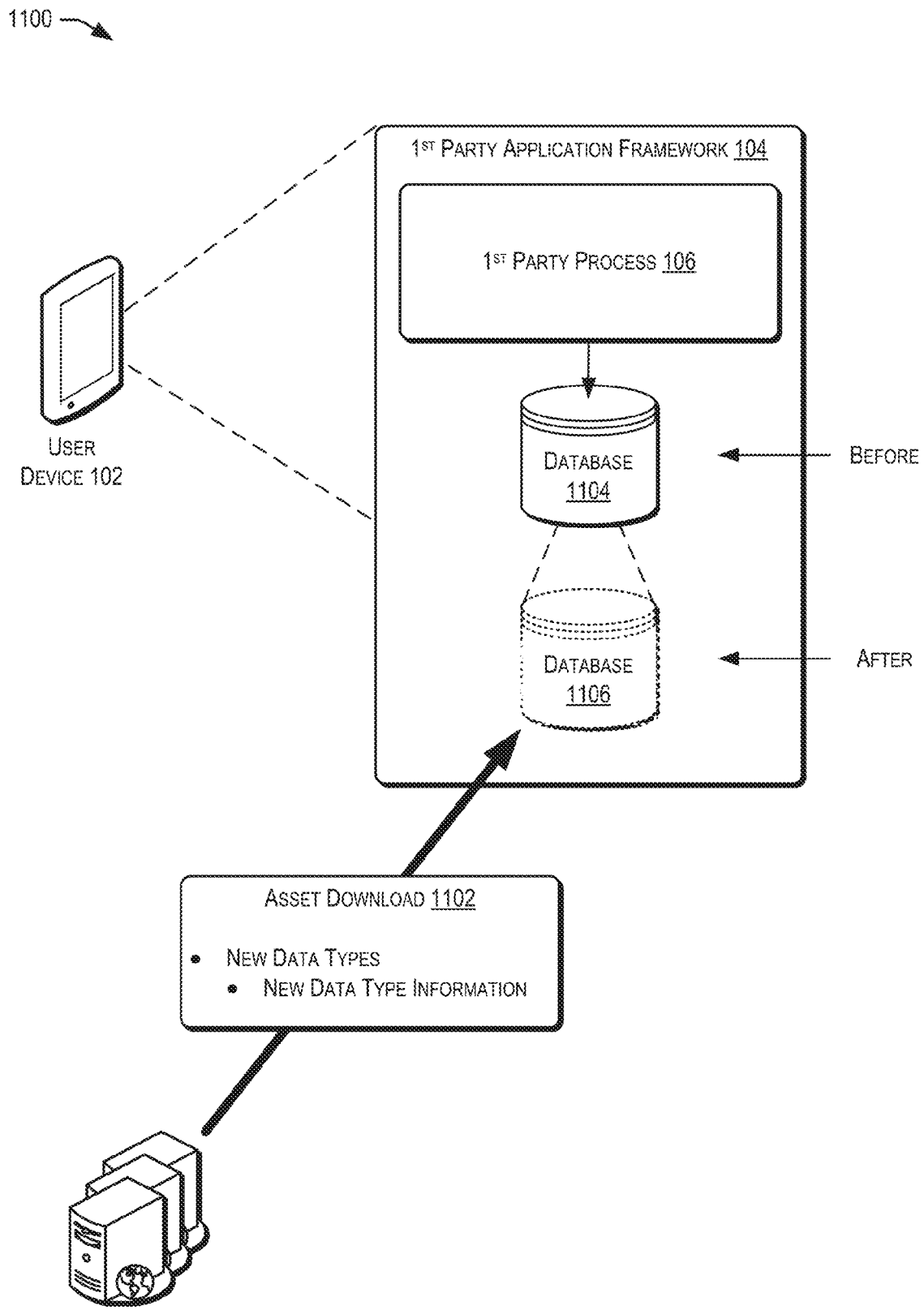
FIG. 11 is another simplified block diagram illustrating another example architecture for managing user information as described herein, according to at least one example.

FIG. 11 illustrates another example architecture 1100 for implementing additional features of the management of personal information from external sources, depicting the user device 102, the first-party application framework 104, and the first-party process 106 of FIG. 1. In some examples, as noted above, one or more service provider computers 304 may be in communication with the first-party application framework 104 and/or the first-party process 106 for providing one or more asset downloads 1102 for extending the functionality of the first-party application framework 104. In other words, an extension framework has been built into the first-party application framework 104 to extend the list of data types originally included with the first-party application framework 104 to include new data types, when desired. For example, if a new product is released on the market (e.g., a new data collection device), and the first-party application framework 104 does not include a data type for managing the data that is collected by this new device (e.g., brisk minutes), the extension framework will be able to enable the new data type to be added to the first-party application framework 104 in between software releases (e.g., in between software code updates for the user device 102. In this way, new data types can be added, managed, and/or utilized without waiting for the next O/S release for the user device 102.

In some examples, a third-party application may ask for a sample type using an API method that includes an identifier. The identifier may be a string that can be predefined and/or baked into the code for existing data types. However, in some examples, once implemented via the asset download 1102 and published, a new string may be utilized to read from and/or write to the new data type. Additionally, once implemented, any application (e.g., third-party applications and/or first-party applications) may utilize the new data type. The asset download 1102 may also include additional information about the new data type including, but not limited to, what type it is (e.g., cumulative or discrete), what string should be used, the identifier, metadata about display, descriptions, etc.

Additionally, in some cases, the first-party process 106 may have the ability to load plug-ins. The first-party process 106 may look for plug-ins in one or more particular directories, and the plug-ins may be configured to enable changes in behavior of the first-party process 106, For example, based at least in part on the device that the plug-ins are installed on, they may enable different behavior changes. In some cases, plug-ins may be utilized for creating differences in behavior (e.g., to make the first-party process 106 behave differently than initially programmed). For example, a plug-in may be utilized to enable the first-party process 106 to register for notifications and/or harvesting different data. Additionally, in some cases, the plug-ins may be utilized for registering the new data types, as described above.

As noted above, a third-party application may ask for a data type by making an API call, and passing in an identifier and/or a "kind." The "kind" may include particular types of the data type (e.g., cumulative, discrete, or category). The identifier, in some cases, may be represented as a string that is passed in via the API, and a data type may be returned to the requesting application. The plug-ins, as noted, can register new data types that adhere to different identifiers so they can store their own data in the database automatically. As such, the first-party process 106 may not need to manage or provide the new data type data to the database 1104.

Instead, the plug-ins may provide the data to the updated database 1106, that includes the new data types and/or both the original data types and the new data types.

In some examples, the asset download 1102 may be a data file (e.g., not executable code) that can be downloaded to the device to provide the appropriate information for extending the data types as described above. In some examples, the asset download 1102 may include data type definition updates. In this way, the user device 102 can download the asset download 1102 and have that information available on the device for access/use by third-party applications. Thus, once downloaded, and used by the first-party process 106 to configure the new data types, the third-party' applications can write to the new data type and read back from it. In some examples, the APIs for reading and writing to the new data type may be extensible so that the executable code for the user device 102 does not need to be changed, but the first-party process 106 can still support the new data type.

The asset download 1102 may be provided by the service provider computers 304 and, as noted, may include all the information for the new data types. In this way, the first-party process 106 may utilize the information in the asset download 1102 to register the new data types identified in the asset download 1102 instead of (or in addition to) using the plug-ins described above. The service provider computers 304 may also publish the identifiers listed in the asset download 1102 to a network resource over a private or public network (e.g., the Internet). In some cases, if an identifier is published before an asset download 1102 is implemented, and an application requests a data type that has not yet been registered with the first-party process 106, then the first-party process 106 may return an error (e.g., "nill" or a null result).

From an implementation perspective, one difference between changing the behavior of the first-party process 106 with plug-ins versus the asset download 1102 is that plug-ins are executable code that include appropriate information for making changes to the functionality, while the asset download 1102 is merely data. As such, code within first-party process 106 may be executed to interpret the data of the asset download 1102 and turn it into actual data types. Any number and/or type of new data types may be added to the first-party application framework 104 and/or utilized by the first-party process 106 even before later software releases for the user device 102. In some cases, data types may also include analysis of the data values (e.g., whether a data value for a particular data type is good or bad for a particular user). This analysis information may also be included in the asset download 1102 and/or published to the network resource for availability to the developers and/or third-party applications. Database 1104 may represent the state of the data types prior to implementation of the asset download 1102 (e.g., with the original data types), while the database 1106 may represent the state of the data types after the implementation of the asset download 1102 (e.g., including the new data types).

Figure 12:
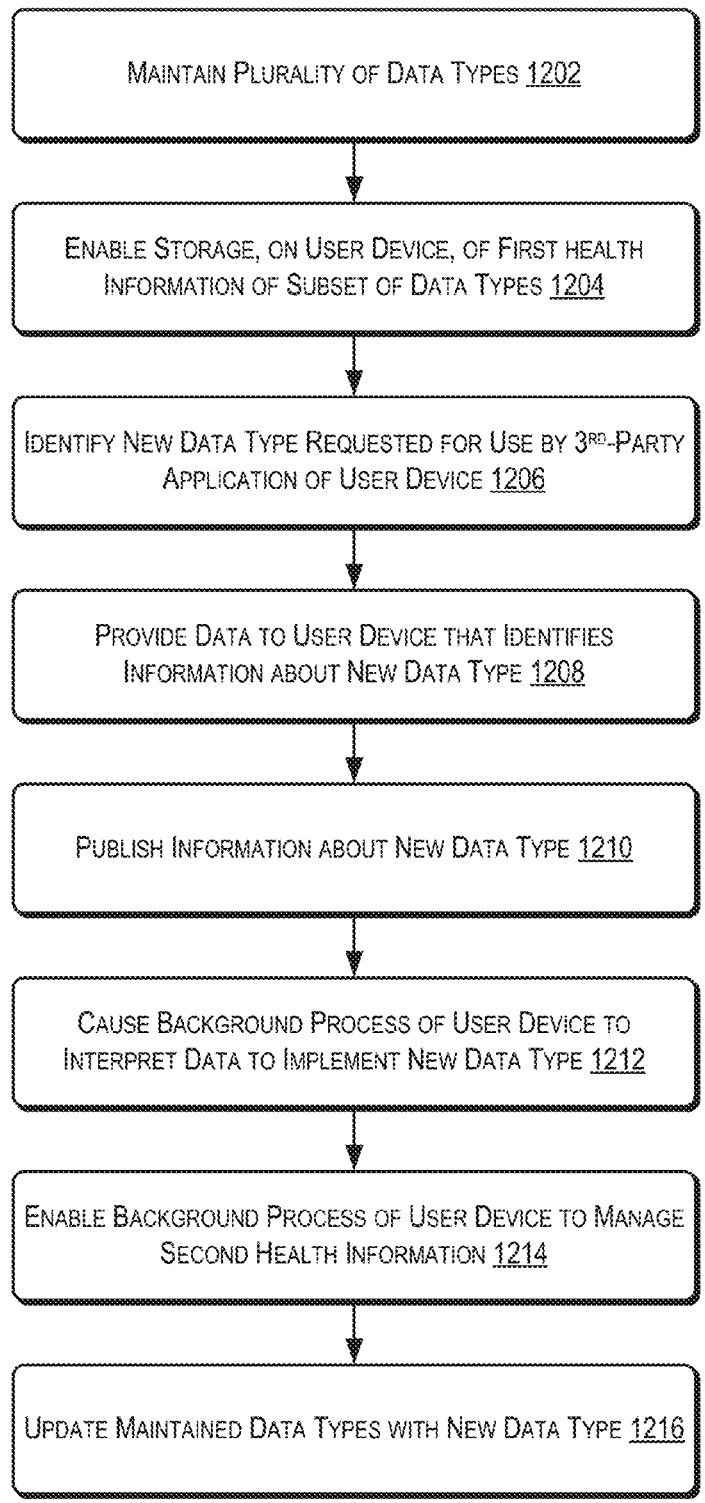
FIG. 12 is another flowchart of a method for managing user information as described herein, according to at least one example.
Figure 13:
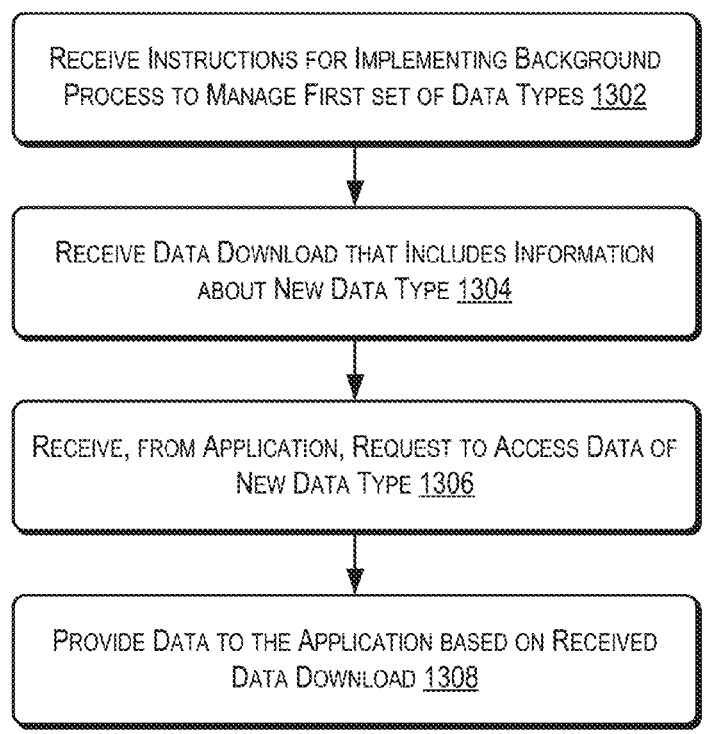
FIG. 13 is another flowchart of a method for managing user information as described herein, according to at least one example.

FIGS. 12 and 13 illustrate example flow diagrams showing processes 1200 and 1300 for managing personal information from external sources, according to at least a few embodiments. In some examples, the service provider computers 304 (e.g., utilizing at least the asset upload module 354 shown in FIG. 3) may perform the process 1200 of FIG. 12. The process 1200 may begin at 1202 by including maintenance of a plurality of data types. As noted, the data types may identify a category or attribute of health information including, but not limited to, weight, glucose levels, steps per minute, heart rate, miles traveled, etc. At 1204, the process 1200 may include enabling storage, on the user device 102, of first health information of a subset of the plurality of data types. In other words, the user device 102 may receive health information corresponding to a single data type, even though multiple data types may exist or be possible.

At 1206, the process 1200 may include identifying a new data type requested for use with a third-party application of the user device 102. In some examples, these new data types may be identified by the service provider computers 302 receiving a request from a developer or other user of the framework. At 1208, the process 122 may include providing data (e.g., the mobile asset) to the user device 102 that identifies the information about the new data type. In some aspects, the process 1200 may also include publishing this information (e.g., the identifiers, descriptions, etc.) at 1210 to a network resource (e.g., a web page or other resource accessible over a network) that may be accessible to the public or at least to developers of third-party applications. At 1212, the process 1200 may include causing a background process (e.g., the first-party process 106) of the user device 102 to interpret the data to implement the new data type. At 1214, the process 1200 may include enabling the background process of the user device to manage second health information (e.g., associated with the new data type). In some examples, the process 1200 may end at 1216, where the service provider computer may update the maintained data types with the new data type. In other words, the service provider computers 304 may update their own tables or databases to include the new data type.

FIG. 13 illustrates another process 1300 for managing personal information from external sources, according to at least a few embodiments. In some examples, the user device 102 (e.g., utilizing at least the extension module 334 shown in FIG. 3) may perform the process 1300 of FIG. 30. The process 1300 may begin at 1302 by including reception of instructions for implementing a background process to manage a first set of data types. In some cases, this first set of data types may be based at least in part on the data types in the original image for the user device 102 and/or for the first-party process 106. At 1304, the process 1300 may include receiving a data download that includes information about the new data type. At 1306, the process 1300 may include receiving, from an application (e.g., a third-party application), a request to access data of the new data type. That is, once the new data type is implemented, third-party applications can make API method calls that include that new data type as a parameter. In some examples, the process 1300 may and at 1308, where the first-party process 106 may provide the data entry corresponding to the new data type to the requesting application.

Figure 14:
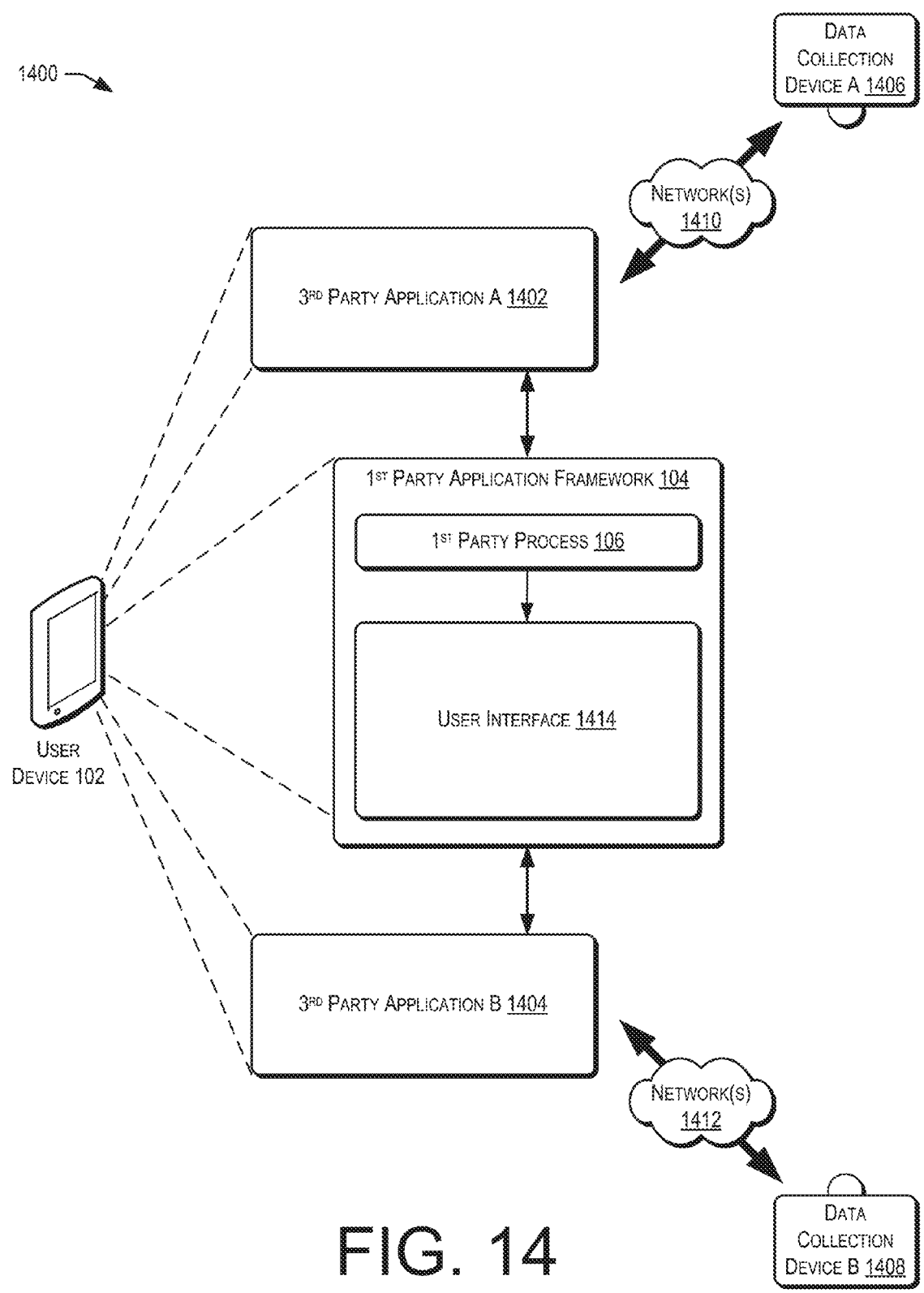
FIG. 14 is another simplified block diagram illustrating another example architecture for managing user information as described herein, according to at least one example.

FIG. 14 illustrates another example architecture 1400 for implementing additional features of the management of personal information from external sources, depicting the user device 102, the first-party application framework 104, and the first-party process 106 of FIG. 1. In some examples, and similar to FIG. 3, one or more third party applications (e.g., third-party application A 1402 and/or third-party application B 1404) may be in communication with the first-party application framework 104 and/or the first-party process 106 for providing user information collected by one or more data collection devices (e.g., data collection device A 1406 and/or data collection device B 1408), respectively. In some examples, the data collection devices 1406, 1408 may be any wearable or mobile device configured to collect activity, health, medical, and/or fitness information about a user. This information may then be provided to one of the third-party applications (e.g., the third-party application A 1402 may receive data from the data collection device A 1406 and/or the data collection device B 1408) via one or more networks 1410 or 1412. Once received by the third-party application A 1402, the information can be provided to the first-party process 106 for storage in a database or other storage system.

While the data collection device A 1406 is shown communicating with the third-party application A 1402 over a network 1412, and the data collection device B 1408 is shown communicating with the third-party application B 1404 over the network 1412, it should be understood that any combination of application-to-device(s) pairings are possible and that such pairings may be facilitated by any number of different or same network connections. Still, when the first-party process 106 is managing input data from a plurality of different applications and/or a plurality of different devices, the first-party process 106 may request priority information from a user of the user device 102. In this way, the user may provide priority information associated with which of the data collection devices 1406, 1408 the user would prefer to track when multiple devices 1406, 1408 are providing data for the same data type and/or for the same time period.

For example, the first-party process 106 may receive data entries from both the data collection device A 1406 and the data collection device B 1408 for the same time period. The data may correspond to a particular data type (e.g., heart rate), yet the data entries may differ slightly (e.g., the two collection devices 1406, 1408 may not be calibrated the same or one might be more sensitive than the other). Instead of tracking both data entries, the first-party process 106 may determine to track only one of the sets of data entries. Similarly, the first-party process 106 may determine to track one set of data for a first set of time and the other set of data of data for a second set of time. The determination of which data entries to track may be based at least in part on a priority set by the user, a type or kind of the data type (e.g., whether it is cumulative or discrete), timing information (e.g., what time the data was received), and/or other information about the data entry.

Additionally, all of the data from the multiple sources may be tracked; however, only some of it may be aggregated into a data record that may be provided or presented to the user via the user device 102. For example, the first-party application framework 104 may be configured to implement a UI 1414 for presenting collected data (e.g., from a single or multiple data collection devices 1406, 1408) and/or aggregated data (e.g., the data record). In some examples, the data record may also be provided to one or more requesting entities (e.g., either or both of the third-party applications 1402, 1404, or other third-party applications. The UI 1414 may be configured to present the aggregated data record or subsets of the data record to the user.

For discrete data, the UI may present a different looking representation of the data than for cumulative data. As such, the first-party process 106 may first identify whether the data to be provided to the UI 1414 is discrete or cumulative. The first-party process 106 may also identify if there is priority information provided by the user. If not, the first-party process 106 may determine priority information based at least in part on previous configurations of the user, historical and/or use information from other users of the device 102 or of other devices (e.g., a probability that the user will use the data collection device 1406 at a particular time), and/or information about accuracy of the respective collection devices 1406, 1408. If priority information exists, the first-party process 106 may use that priority information to determine which collected data for a single data type should be included in the data record for each time period or for each time segment of the time period (e.g., each second of the 5 minute window of collected data, etc.). The priority information may be configured via the UI 1414, such that the user may slide, drag, or otherwise virtually move the sources (e.g., the data collection devices 1406, 1408) up and down to identify a preferred priority. As desired, the priority information and the received data entries may correspond to any number of data collection devices and/or applications.

The collected data may be segmented for each time period such that data is represented in a meaningful manner. For example, if a person never takes more than a single step per millisecond, using milliseconds as the segmentation for steps would probably not provide meaningful results. However, if the lower bounds for steps were half a second (e.g., when someone is running) and 2 seconds (e.g., when someone is walking very slow), then the segments for steps should be somewhere between 0.5 and 2 seconds for a particular time window (e.g., an entire day or at least the hours that the user spends awake). As such, historical and/or use information for each data type may be collected and analyzed to automatically identify appropriate segment bounds. In some cases, this may avoid double counting, for example, when multiple data sources are providing the same data entries for the same segment. In other examples, predefined segments may be used for each data type and/or information about the user collected from other sources, devices, applications, etc.

The first-party process 106 and/or the first-party application framework 104 may provide API methods for third parties (e.g., the third-party application 1402) to utilize to retrieve the aggregated data records. In this way, the third-party application 1402 may be able to customize a request for aggregated data over a particular period of time and/or for a particular data type. As desired, the first-party process 106 may respond to the API method calls by providing an aggregated data record that includes data collected from sources other than the requestor (e.g., other than the third-party application 1402). This may enable one application to receive an aggregated data record that is not solely based on the data the data provided by that application. Additionally, the UI 1414 may be configured to provide cumulative and/or discrete data for multiple data sources to a user or other application.

Figure 15:
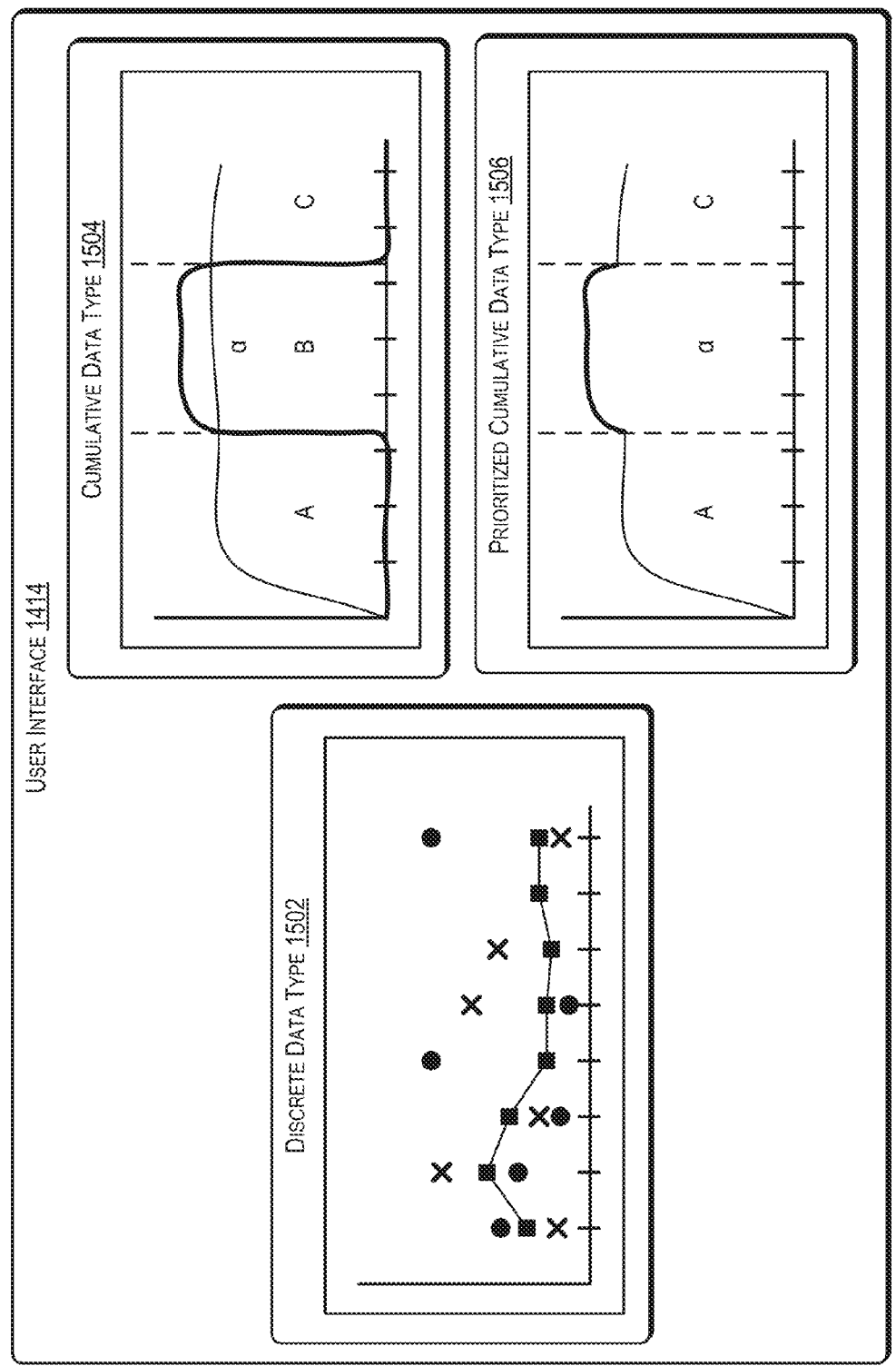
FIG. 15 is a simplified block diagram illustrating an example user interface for presenting user information as described herein, according to at least one example.

FIG. 15 illustrates several example UI renderings within the UI 1414 of FIG. 14. For example, for discrete data type presentations 1502, the UI 1414 may be configured to represent each data entry as a data point on a time graph. As shown, for the discrete data type presentation 1502, there may be multiple data entries for each segment of the total time period. For example, a user may have three different devices collecting their weight over the course of a day, week, month, etc. At each segment, the discrete data type presentation 1502 may include each data entry received by the first-party process 106 from the three different sources. Since weight is not a data type that would be added up over time (e.g., it is discrete), it may be appropriate to present each different data point for each segment. In some examples, a prioritized source may be identified by a line or other interface object/element that highlights the data points from that source. Here, the line connecting the square points on the presentation 1502 is one example of a way to represent priority or a preferred data source.

In some examples, when the data is cumulative, the data may be summed or otherwise added up over the entire time period. As shown in the cumulative data type presentation

1504, this may cause a double counting problem when multiple sources provide data for the same time segments. For example, over the first third of the time period, the first-party process 106 may only have received data from a first source (e.g., A number of steps). For a cumulative data type (e.g., steps walked), the data entries at each segment may be added together to get a total. Similarly, at the last third of the time period, the first-party process 106 may also have only received data from the first source (e.g., C number of steps). However, if two sources provided step data during the middle third of the time period, adding both B number of steps and alpha number of steps would not provide an accurate total step count because the number of steps during that time period would be double counted or at least counted from two different sources. As such, using the priority information collected from the user, the UI 1414 may be able to present a piecemeal representation such as the prioritized cumulative data type presentation 1506. In this presentation 1506, the alpha number of steps may have been identified as the user's prioritized data source for this subset of the time period. As such, only alpha number of steps (e.g., coming from one source) is shown during that subset of the time period, while A and C number of steps (e.g., coming from a different source). The total number of steps aggregated over the time period in this presentation 1506 may be A+alpha+C, as opposed to A+B+alpha+C from the cumulative data type presentation 1504.

Figure 16:
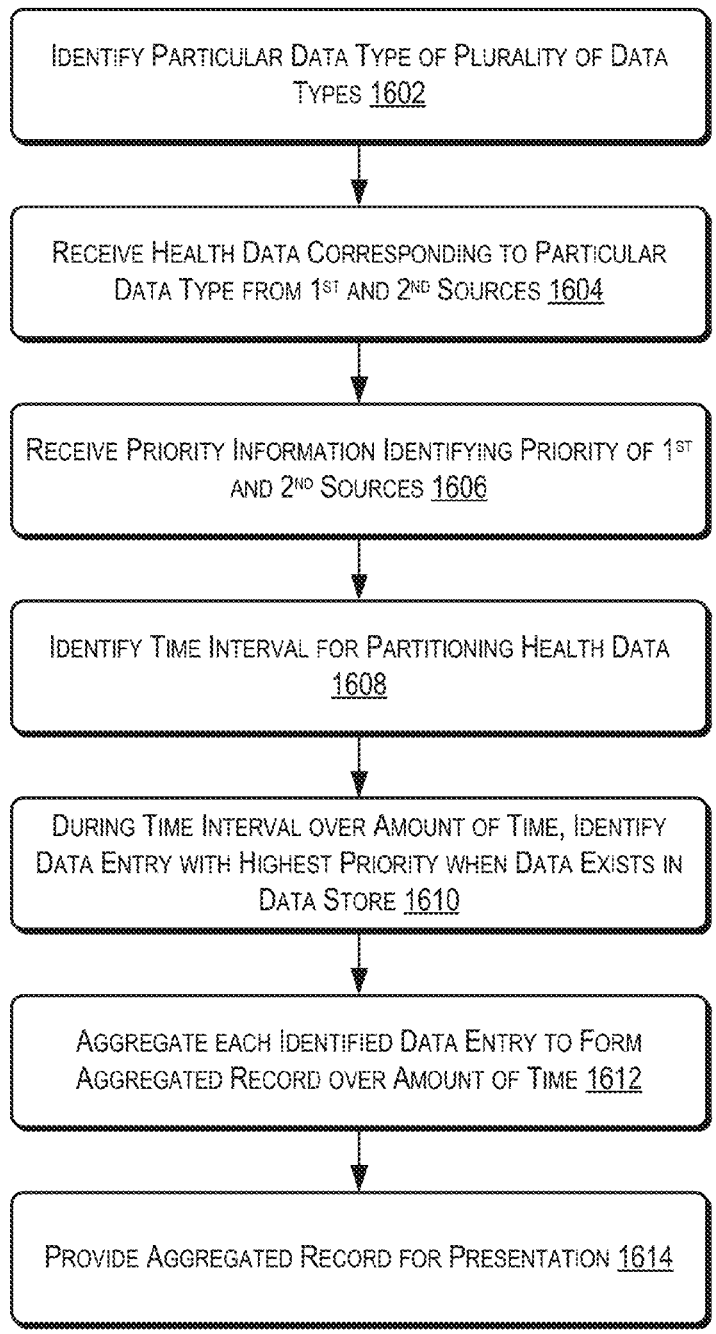
FIG. 16 is another flowchart of a method for managing user information as described herein, according to at least one example.
Figure 17:
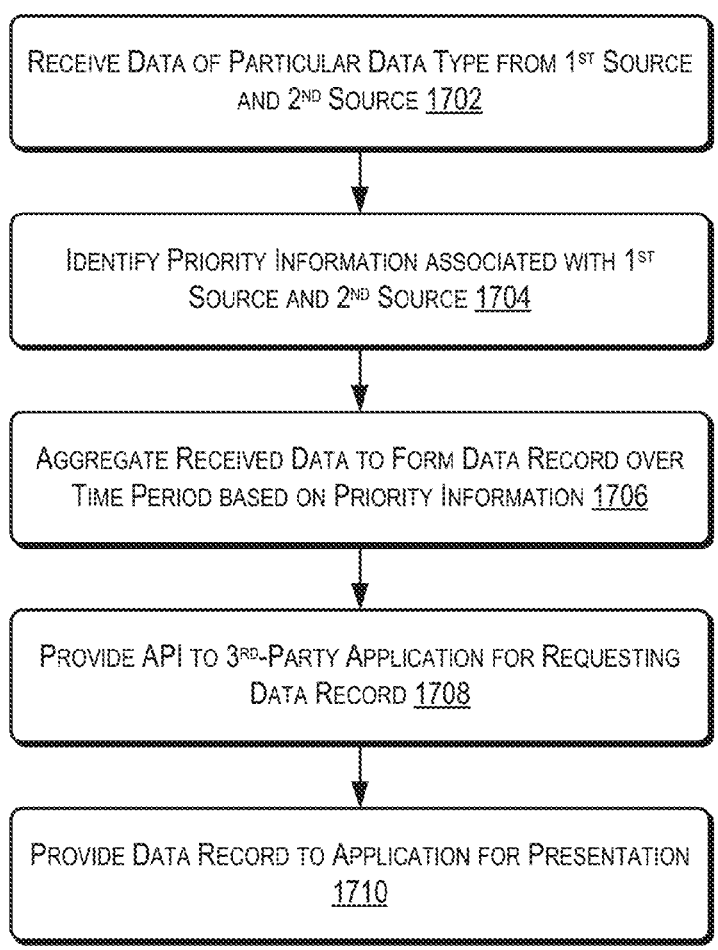
FIG. 17 another flowchart of a method for managing user information as described herein, according to at least one example.

FIGS. 16 and 17 illustrate example flow diagrams showing processes 1600 and 1700 for managing personal information from external sources, according to at least a few embodiments. In some examples, the user device 102 (e.g., utilizing at least the aggregation module 340 shown in FIG. 3) may perform the process 1600 of FIG. 16. The process 1600 may begin at 1602 by including identification of a particular data type of a plurality of data types. Identification of the particular data type may include identifying the data type itself (e.g., number of steps, weight, heart rate, etc.) or identifying a type or kind of the data type (e.g., cumulative or discrete). At 1604, the process 1600 may include receiving health data corresponding to particular the particular data entry from at least a first data source and a second data source. The data sources may be third-party applications, other (e.g., first-party) applications, and/or data collection devices. At 1606, the process 1600 may include receiving priority information identifying a priority of the first and second sources. This priority information may be received via a UI where the user can virtually move icons or other source identifiers up and down to indicate position, or it may be done in code, or using other techniques such as, but not limited to, check boxes, radio buttons, drop down lists, text entry (e.g., 1, 2, 3, etc.), or the like.

At 1608, the process 1600 may include identifying a time interval for partitioning the health data. These partitions (also referred to as segments) may be based at least in part on user information, data type information, historical and/or use data, or the like. At 1610, the process 1600 may include identifying a data entry corresponding to a source with the highest priority during each time interval or segment. In some examples, this may only apply when a data entry exists for that segment. At 1612, the process 1600 may include aggregating each identified data record over the amount of time (e.g., the day, an hour, etc.). In some cases, the process 1600 may end at 1614, where the process 1600 may include providing the aggregated data record for presentation (e.g., to the user).

FIG. 17 illustrates another process 1700 for managing personal information from external sources, according to at least a few embodiments. In some examples, the user device 102 (e.g., utilizing at least the aggregation module 340 shown in FIG. 3) may perform the process 1700 of FIG. 17. The process 1700 may begin at 1702 by including receiving data of a particular data type from a first source and a second source. At 1704, the process 1700 may include identifying priority information associated with the first source and the second source. For example, the priority information may indicate which of the first or second source, the user prefers to view data from when they both provide data for the same data type. At 1706, the process 1700 may include aggregating the received data to form a data record over a period of time. The aggregated data record may be based at least in part on the priority information and/or a probability that the user will prefer (and/or use) one of the sources over the other one. At 1708, the process 1700 may include providing an API to the third-party applications for request the aggregated data record. The process 1700 may end at 1710, where the process 1700 may include providing the data record to an application for presentation. A UI may be provided that represents the aggregated data record such as, but not limited to, the prioritized cumulative data type presentation 1506 or something similar.

Illustrative methods and systems for managing user device connections are described above. Some or all of these systems and methods may, but need not, be implemented at least partially by architectures such as those shown at least in FIGS. 1-17 above. While many of the embodiments are described above with reference to personal and/or health-related information, it should be understood any time of user information or non-user information (e.g., data of any type) may be managed using these techniques. Further, in the foregoing description, various non-limiting examples were described. For purposes of explanation, specific configurations and details are set forth in order to provide a thorough understanding of the examples. However, it should also be apparent to one skilled in the art that the examples may be practiced without the specific details. Furthermore, well-known features were sometimes omitted or simplified in order not to obscure the example being described.

The various embodiments further can be implemented in a wide variety of operating environments, which in some cases can include one or more user computers, computing devices or processing devices which can be used to operate any of a number of applications. User devices (e.g., client devices) can include any type of general purpose personal computer such as, but not limited to, desktop or laptop computers running a standard operating system, as well as cellular, wireless, and/or handheld devices running mobile software and capable of supporting a number of networking and messaging protocols. These devices can also include other electronic devices, such as dummy terminals, thin-clients, gaming systems, or other devices capable of communicating via a network.

Most embodiments utilize at least one network that would be familiar to those skilled in the art for supporting communications using any of a variety of commercially-available protocols, such as TCP/IP, OSI, FTP, NFS, CIFs, and AppleTalk. The network can be, for example, a local area network, a wide-area network, a virtual private network, the Internet, an intranet, an extranet, a public switched telephone network, an infrared network, a wireless network, and any combination thereof.

The environment can include a variety of data stores and other memory and storage media as discussed above. These can reside in a variety of locations, such as on a storage medium local to (and/or resident in) one or more of the computers. Alternatively, the memory can be remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as desired.

The system and various devices may also include one or more software applications, modules, services, or other elements located within at least one working memory device, including an operating system and application programs, such as a client application or browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the disclosure. However, other embodiments of the disclosure may be directed to specific embodiments relating to each individual aspect, or specific combinations of these individual aspects The above description of exemplary embodiments of the disclosure has been presented for the purposes of illustration and description. It is not intended to be exhaustive or to limit the disclosure to the precise form described, and many modifications and variations are possible in light of the teaching above. The embodiments were chosen and described in order to best explain the principles of the disclosure and its practical applications to thereby enable others skilled in the art to best utilize the disclosure in various embodiments and with various modifications as are suited to the particular use contemplated.

All references, including publications, patent applications, and patents, cited herein are hereby incorporated by reference to the same extent as if each reference were individually and specifically indicated to be incorporated by reference and were set forth in its entirety herein.

What is claimed is:

1. A computer-implemented method, comprising:
identifying, by a computer system, a particular data type of a plurality of data types to manage;
receiving health data corresponding to the particular data type from at least a first source and a second source of a plurality of data sources;
receiving priority information identifying a priority of first source and the second source;
identifying a time interval for partitioning the health data by the plurality of data sources;
during each identified time interval over an amount of time, identifying a data entry for the particular data type with a highest identified priority when the data entry exists in a data store configured to maintain the received health data corresponding to the particular data type; and
aggregating each identified data entry to form an aggregated record for the particular data type over the amount of time.

2. The computer-implemented method of claim 1, further comprising providing the aggregated record to a user device for presentation within a user interface to a user.

3. The computer-implemented method of claim 1, further comprising receiving a request from the first source for the aggregated record that at least includes the received health data from the second source.

4. The computer-implemented method of claim 1, further comprising identifying a type of the particular data type based at least in part on metadata associated with received health data.

5. The computer-implemented method of claim 4, wherein the aggregated record only includes each identified data entry corresponding to the highest identified priority when the identified type is cumulative.

6. The computer-implemented method of claim 4, wherein the aggregated record includes each identified data entry corresponding to the highest identified priority and other identified data entries for the identified time period when the identified type is discrete.

7. A system, comprising:
a memory configured to store computer-executable instructions; and
a processor in communication with the memory configured to execute the computer-executable instructions to at least:
receive data of a particular data type from a plurality of sources, the data including at least respective time stamps;
aggregate the received data to form a data record for a period of time based at least in part on the respective time stamps; and
provide the data record to at least one application configured to present a user interface representing the aggregated data of the plurality of sources.

8. The system of claim 7, wherein the at least one application is a particular one of the plurality of sources, and wherein the data record includes at least one data point not received from the particular one of the plurality of sources.

9. The system of claim 7, wherein at least one of the plurality of sources comprises a third-party application or a first-party application.

10. The system of claim 9, wherein the received data is based at least in part on metrics collected by a data collection device associated with at least one of the third-party application or the first-party application.

11. The system of claim 7, wherein the processor is further configured to execute the computer-executable instructions to at least identify priority information for at least a subset of the plurality of sources and a time interval for the period of time.

12. The system of claim 11, wherein the processor is further configured to execute the computer-executable instructions to at least identify a data entry for the particular data type with a highest identified priority for each time interval.

13. The system of claim 12, wherein the provided data record only includes each identified data entry corresponding to the highest identified priority when the particular data type is cumulative.

14. The system of claim 7, wherein the provided data record includes data entries corresponding to the particular data type from the plurality of sources for individual time intervals of the period of time, wherein at least one time interval of the individual time intervals includes a plurality of different data entries, and wherein at least one of the plurality of data entries is from a different source of the plurality of sources.

15. A computer-readable storage medium storing computer-executable instructions that, when executed by a processor, configure the processor to perform operations comprising:
receiving data of a particular data type from at least a first data source and a second data source;
identifying priority information associated with the first data source and the second data source;
aggregating, based at least in part on the priority information, the received data to form a data record over a period of time; and
providing the data record to at least one application configured to present a user interface representing the aggregated data of the first data source and the second data source.

16. The one or more computer-readable media of claim 15, wherein the data record represents individual data entries of the particular data type for each of a plurality of time intervals during the period of time.

17. The computer-readable medium of claim 16, wherein a length of the plurality of time intervals is determined based at least in part on at least one of the particular data type, an activity associated with the particular data type, or historical information associated with a user of the at least one application.

18. The computer-readable medium of claim 15, wherein the identified priority information is determined based at least in part on at least one of a preference of a user, historical behavior of the user, or activity behavior associated with the first data source or the second data source.

19. The computer-readable medium of claim 15, wherein the at least one application comprises a third-party application configured to provide a user interface corresponding to the data record to a user of the third-party application.

20. The computer-readable medium of claim 19, wherein the operations further comprise providing an application programming interface method to the third-party application for requesting the data record, the data record including at least some health information of the user not provided by the third-party application.

* * * * *

UNITED STATES PATENT AND TRADEMARK OFFICE
CERTIFICATE OF CORRECTION

PATENT NO.       : 9,582,643 B2
APPLICATION NO.  : 14/499519
DATED            : February 28, 2017
INVENTOR(S)      : Daniel S. Keen, Justin S. Rushing and Jay C. Blahnik It is certified that error appears in the above-identified patent and that said Letters Patent is hereby corrected as shown below:

In the Claims

Claim 1 (Column 26, Line 47):
Delete "of first" and insert --of the first--.

Claim 4 (Column 27, Line 3):
Delete "with received" and insert --with the received--.

Signed and Sealed this
Nineteenth Day of June, 2018

Andrei Iancu
*Director of the United States Patent and Trademark Office*